(12) United States Patent
Bar-Yoseph et al.

(10) Patent No.: US 12,408,905 B2
(45) Date of Patent: *Sep. 9, 2025

(54) TISSUE CONTAINMENT DEVICE FOR USE IN SURGICAL PROCEDURES

(71) Applicant: Ark Surgical Ltd., Nazareth (IL)

(72) Inventors: Gill Bar-Yoseph, Haifa (IL); David Bleicher, Tel-Aviv (IL)

(73) Assignee: Ark Surgical Ltd., Nazareth (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/670,562

(22) Filed: Feb. 14, 2022

(65) Prior Publication Data
US 2022/0160342 A1 May 26, 2022

Related U.S. Application Data

(63) Continuation of application No. 16/310,435, filed as application No. PCT/IL2017/050674 on Jun. 18, 2017, now Pat. No. 11,253,239.
(Continued)

(51) Int. Cl.
*A61B 17/00* (2006.01)
*A61B 17/221* (2006.01)
(Continued)

(52) U.S. Cl.
CPC ...... *A61B 17/00234* (2013.01); *A61B 17/221* (2013.01); *A61B 90/06* (2016.02);
(Continued)

(58) Field of Classification Search
CPC . A61B 17/00234; A61B 17/221; A61B 90/06; A61B 90/08; A61B 2017/00287;
(Continued)

(56) References Cited

U.S. PATENT DOCUMENTS

| 3,634,938 A | 1/1972 | Hutchinson |
| 4,478,580 A | 10/1984 | Barrut |

(Continued)

FOREIGN PATENT DOCUMENTS

| AU | 2012202287 | 5/2012 |
| CN | 1939224 | 4/2007 |

(Continued)

OTHER PUBLICATIONS

International Search Report and the Written Opinion Dated Jul. 6, 2022 From the International Searching Authority Re. Application No. PCT/IL2021/051499. (24 Pages).
(Continued)

*Primary Examiner* — Brigid K Byrd

(57) ABSTRACT

A tissue containment device (10) for isolating tissue from surrounding tissue during a surgical procedure to remove the tissue includes a bag (12) formed by one or more walls (14) defining a containment compartment (16) and an opening (18) for accessing the containment compartment. Each wall (14) is formed from at least two layers including an inner layer (20) facing the containment compartment and an outer layer (22) facing outwards from bag (12). The layers define between them one or more inflatable volumes (24). Layers (20) and (22) are interconnected at spaced-apart connection regions (28) that are arranged such that, when a fluid is introduced into the inflatable volumes (24), regions of the at least two layers between the connection regions form wall cavity regions surrounding an internal volume of the containment compartment.

28 Claims, 17 Drawing Sheets

Related U.S. Application Data

(60) Provisional application No. 62/350,745, filed on Jun. 16, 2016.

(51) Int. Cl.
*A61B 90/00* (2016.01)
*A61B 17/22* (2006.01)

(52) U.S. Cl.
CPC .... *A61B 90/08* (2016.02); *A61B 2017/00287* (2013.01); *A61B 2017/00818* (2013.01); *A61B 2017/00955* (2013.01); *A61B 2017/22062* (2013.01); *A61B 2017/2215* (2013.01); *A61B 2090/064* (2016.02); *A61B 2090/08021* (2016.02); *A61B 2090/0809* (2016.02)

(58) Field of Classification Search
CPC .... A61B 2017/22062; A61B 2090/064; A61B 2090/08021; A61B 2090/0809
See application file for complete search history.

(56) References Cited

U.S. PATENT DOCUMENTS

| | | | |
|---|---|---|---|
| 4,571,180 A | 2/1986 | Kulick | |
| 4,665,621 A | 5/1987 | Ackerman et al. | |
| 4,764,114 A | 8/1988 | Jeffcoat et al. | |
| 4,790,751 A | 12/1988 | Reinhardt et al. | |
| 4,873,651 A | 10/1989 | Raviv | |
| 4,883,425 A | 11/1989 | Zimble | |
| 4,935,635 A | 6/1990 | O'Harra | |
| 5,051,823 A | 9/1991 | Cooper et al. | |
| 5,176,687 A | 1/1993 | Hasson et al. | |
| 5,178,537 A | 1/1993 | Currie | |
| 5,215,521 A | 6/1993 | Cochran et al. | |
| 5,224,049 A | 6/1993 | Mushabac | |
| 5,230,621 A | 7/1993 | Jacoby | |
| 5,244,387 A | 9/1993 | Fuierer | |
| 5,257,184 A | 10/1993 | Mushabac | |
| 5,308,327 A | 5/1994 | Heaven et al. | |
| 5,313,053 A | 5/1994 | Koenck et al. | |
| 5,318,442 A | 6/1994 | Jeffcoat et al. | |
| 5,320,462 A | 6/1994 | Johansson et al. | |
| 5,361,752 A * | 11/1994 | Moll | A61B 17/0218 604/908 |
| 5,368,597 A | 11/1994 | Pagedas | |
| 5,372,502 A | 12/1994 | Massen et al. | |
| 5,423,677 A | 6/1995 | Brattesani | |
| 5,524,633 A | 6/1996 | Heaven et al. | |
| 5,618,296 A | 4/1997 | Sorensen et al. | |
| 5,743,731 A | 4/1998 | Lares et al. | |
| 5,850,289 A | 12/1998 | Fowler et al. | |
| 5,862,559 A | 1/1999 | Hunter | |
| 5,897,509 A | 4/1999 | Toda et al. | |
| 5,919,129 A | 7/1999 | Vandre | |
| 5,944,523 A | 8/1999 | Badoz | |
| 5,947,992 A * | 9/1999 | Zadini | A61F 5/4553 606/191 |
| 5,969,321 A | 10/1999 | Danielson et al. | |
| 5,993,209 A | 11/1999 | Matoba et al. | |
| 6,000,939 A | 12/1999 | Ray et al. | |
| 6,007,333 A | 12/1999 | Callan et al. | |
| 6,116,899 A | 9/2000 | Takeuchi | |
| 6,142,936 A | 11/2000 | Beane et al. | |
| 6,179,611 B1 | 1/2001 | Everett et al. | |
| 6,276,934 B1 | 8/2001 | Rakocz | |
| 6,309,219 B1 | 10/2001 | Robert | |
| 6,406,440 B1 | 6/2002 | Stefanchik | |
| 6,423,803 B1 | 7/2002 | Nagpal et al. | |
| 6,468,079 B1 | 10/2002 | Fischer et al. | |
| 6,589,268 B1 * | 7/2003 | McEwen | A61B 17/1355 606/202 |
| 6,819,318 B1 | 11/2004 | Geng | |
| 6,885,464 B1 | 4/2005 | Pfeiffer et al. | |
| 6,942,679 B1 * | 9/2005 | Terai | A61M 25/1002 606/192 |
| 7,041,056 B2 | 5/2006 | Deslauriers et al. | |
| 7,056,329 B2 | 6/2006 | Kerr | |
| 7,097,648 B1 | 8/2006 | Globerman et al. | |
| 7,235,066 B1 * | 6/2007 | Narini | A61H 35/00 128/853 |
| 7,346,417 B2 | 3/2008 | Lueth et al. | |
| 7,494,338 B2 | 2/2009 | Durbin et al. | |
| 7,625,335 B2 | 12/2009 | Deichmann et al. | |
| 7,668,583 B2 | 2/2010 | Fegert et al. | |
| 7,766,823 B2 | 8/2010 | Moll et al. | |
| 7,813,591 B2 | 10/2010 | Paley et al. | |
| 8,280,152 B2 | 10/2012 | Thiel et al. | |
| 8,287,561 B2 | 10/2012 | Nunez et al. | |
| 8,371,848 B2 | 2/2013 | Okawa et al. | |
| 8,744,194 B2 | 6/2014 | Kawasaki et al. | |
| 8,764,646 B2 | 7/2014 | Grundeman | |
| 8,936,470 B2 | 1/2015 | Pruckner et al. | |
| 9,137,511 B1 | 9/2015 | LeGrand, III et al. | |
| 9,179,987 B2 | 11/2015 | Goodacre | |
| 9,463,081 B2 | 10/2016 | Urakabe | |
| 9,522,054 B2 | 12/2016 | Kim et al. | |
| 9,603,675 B2 | 3/2017 | Pruckner | |
| 9,918,805 B2 | 3/2018 | Pruckner | |
| 10,136,970 B2 | 11/2018 | Pesach | |
| 10,182,875 B2 | 1/2019 | Yates et al. | |
| 10,206,666 B2 | 2/2019 | Dickson et al. | |
| 10,226,599 B2 | 3/2019 | Schaffer | |
| 10,299,880 B2 | 5/2019 | Ramirez Luna et al. | |
| 10,470,846 B2 | 11/2019 | Kopelman et al. | |
| 10,695,150 B2 | 6/2020 | Kopelman et al. | |
| 2002/0103420 A1 | 8/2002 | Coleman et al. | |
| 2002/0133096 A1 | 9/2002 | Toda et al. | |
| 2004/0087937 A1 | 5/2004 | Eggers et al. | |
| 2004/0097792 A1 | 5/2004 | Moll et al. | |
| 2004/0106868 A1 | 6/2004 | Liew et al. | |
| 2004/0158261 A1 | 8/2004 | Vu | |
| 2005/0116673 A1 | 6/2005 | Carl et al. | |
| 2006/0154198 A1 | 7/2006 | Durbin et al. | |
| 2007/0037125 A1 | 2/2007 | Maev et al. | |
| 2007/0042315 A1 | 2/2007 | Boutoussov et al. | |
| 2007/0064242 A1 | 3/2007 | Childers | |
| 2007/0065782 A1 | 3/2007 | Maschke | |
| 2007/0172112 A1 | 7/2007 | Paley et al. | |
| 2007/0225744 A1 | 9/2007 | Nobles et al. | |
| 2007/0260231 A1 | 11/2007 | Rose et al. | |
| 2008/0002011 A1 | 1/2008 | Mizutani et al. | |
| 2008/0002869 A1 | 1/2008 | Scharlack et al. | |
| 2008/0038688 A1 | 2/2008 | Kopelman et al. | |
| 2008/0051817 A1 | 2/2008 | Leahy | |
| 2008/0145817 A1 | 6/2008 | Brennan et al. | |
| 2008/0160477 A1 | 7/2008 | Stookey et al. | |
| 2008/0201101 A1 | 8/2008 | Hebert et al. | |
| 2008/0261165 A1 | 10/2008 | Steingart et al. | |
| 2009/0017416 A1 | 1/2009 | Nguyen et al. | |
| 2009/0043314 A1 | 2/2009 | Sevensson et al. | |
| 2009/0061383 A1 | 3/2009 | Kang | |
| 2009/0087050 A1 | 4/2009 | Gandyra | |
| 2009/0306506 A1 | 12/2009 | Heger et al. | |
| 2009/0326383 A1 | 12/2009 | Barnes et al. | |
| 2010/0047733 A1 | 2/2010 | Nahlieli | |
| 2010/0092908 A1 | 4/2010 | Rothenwaender et al. | |
| 2010/0189341 A1 | 7/2010 | Oota et al. | |
| 2010/0238279 A1 | 9/2010 | Thoms et al. | |
| 2010/0239136 A1 | 9/2010 | Gandyra et al. | |
| 2010/0239996 A1 | 9/2010 | Ertl | |
| 2010/0268069 A1 | 10/2010 | Liang | |
| 2010/0268071 A1 | 10/2010 | Kim | |
| 2010/0305435 A1 | 12/2010 | Magill | |
| 2011/0087235 A1 * | 4/2011 | Taylor | A61B 17/00234 606/114 |
| 2011/0184245 A1 | 7/2011 | Xia et al. | |
| 2011/0184432 A1 * | 7/2011 | Parihar | A61B 17/00234 606/114 |
| 2011/0190781 A1 | 8/2011 | Collier et al. | |
| 2011/0301419 A1 | 12/2011 | Craft et al. | |
| 2012/0015329 A1 | 1/2012 | Gross et al. | |
| 2012/0040305 A1 | 2/2012 | Karazivan et al. | |

(56) References Cited

U.S. PATENT DOCUMENTS

| | | |
|---|---|---|
| 2012/0046536 A1 | 2/2012 | Cheung et al. |
| 2012/0097002 A1 | 4/2012 | Thiedig |
| 2012/0179281 A1 | 7/2012 | Steingart et al. |
| 2012/0189182 A1 | 7/2012 | Liang et al. |
| 2012/0270177 A1 | 10/2012 | Nakashima et al. |
| 2012/0271176 A1 | 10/2012 | Moghaddam et al. |
| 2013/0000666 A1 | 1/2013 | Hu |
| 2013/0017507 A1 | 1/2013 | Moffson et al. |
| 2013/0027515 A1 | 1/2013 | Vinther et al. |
| 2013/0188012 A1 | 7/2013 | Bellis et al. |
| 2013/0209953 A1 | 8/2013 | Arlinsky et al. |
| 2013/0253278 A1 | 9/2013 | Smith |
| 2013/0273492 A1 | 10/2013 | Suttin, Sr. et al. |
| 2014/0066784 A1 | 3/2014 | Yokota |
| 2014/0093835 A1 | 4/2014 | Levin |
| 2014/0111616 A1 | 4/2014 | Blayvas |
| 2014/0120492 A1 | 5/2014 | Ioannidis et al. |
| 2014/0120493 A1 | 5/2014 | Levin |
| 2014/0146142 A1 | 5/2014 | Duret et al. |
| 2014/0178832 A1 | 6/2014 | Choi et al. |
| 2014/0194696 A1 | 7/2014 | Fischvogt |
| 2014/0199650 A1 | 7/2014 | Moffson et al. |
| 2014/0221819 A1 | 8/2014 | Sarment |
| 2014/0248577 A1 | 9/2014 | Tahmasebi et al. |
| 2014/0275801 A1 | 9/2014 | Menchaca et al. |
| 2014/0276055 A1 | 9/2014 | Barthe et al. |
| 2014/0309523 A1 | 10/2014 | Daon et al. |
| 2014/0330285 A1 | 11/2014 | Rosenblatt et al. |
| 2014/0343395 A1 | 11/2014 | Choi et al. |
| 2015/0015701 A1 | 1/2015 | Yu |
| 2015/0118638 A1 | 4/2015 | Cowburn |
| 2015/0182299 A1 | 7/2015 | Koubi et al. |
| 2015/0223910 A1 | 8/2015 | Pruckner |
| 2015/0223916 A1 | 8/2015 | Kim et al. |
| 2015/0229911 A1 | 8/2015 | Ge et al. |
| 2015/0297254 A1 | 10/2015 | Sullivan et al. |
| 2015/0348320 A1 | 12/2015 | Pesach et al. |
| 2016/0100857 A1 | 4/2016 | Wachli et al. |
| 2016/0120615 A1 | 5/2016 | Scurtescu |
| 2016/0259515 A1 | 9/2016 | Sabina et al. |
| 2016/0262856 A1 | 9/2016 | Atiya et al. |
| 2016/0270878 A1 | 9/2016 | Fulton, III |
| 2016/0302783 A1* | 10/2016 | Greenberg ....... A61B 17/00234 |
| 2016/0338682 A1 | 11/2016 | Hoyte et al. |
| 2016/0338803 A1 | 11/2016 | Pesach |
| 2017/0007377 A1 | 1/2017 | Pesach et al. |
| 2017/0079708 A1* | 3/2017 | Gilbert ............... A61B 18/1206 |
| 2017/0128059 A1 | 5/2017 | Coe et al. |
| 2017/0202483 A1 | 7/2017 | Sorimoto et al. |
| 2017/0252026 A1 | 9/2017 | Gupta et al. |
| 2018/0008250 A1* | 1/2018 | Joseph ............. A61B 17/00234 |
| 2018/0049830 A1 | 2/2018 | Yates et al. |
| 2018/0360481 A1 | 12/2018 | Bonadio et al. |
| 2019/0117241 A1 | 4/2019 | Sherman et al. |
| 2019/0192262 A1 | 6/2019 | Pesach |
| 2019/0247033 A1 | 8/2019 | Yaari |
| 2019/0262098 A1 | 8/2019 | Pesach et al. |
| 2019/0328376 A1 | 10/2019 | Bar-Yoseph et al. |
| 2019/0343598 A1 | 11/2019 | Knobel et al. |
| 2020/0060550 A1 | 2/2020 | Pesach et al. |
| 2020/0155285 A1 | 5/2020 | Pesach et al. |
| 2020/0268410 A1 | 8/2020 | Yaari et al. |
| 2022/0071737 A1 | 3/2022 | Pesach et al. |
| 2024/0050123 A1 | 2/2024 | Tori et al. |

FOREIGN PATENT DOCUMENTS

| | | |
|---|---|---|
| CN | 101677757 | 3/2010 |
| EP | 1707130 | 10/2006 |
| EP | 1901033 | 3/2008 |
| EP | 2165674 | 3/2010 |
| EP | 2485664 | 8/2012 |
| EP | 2630929 | 8/2013 |
| ES | 2115544 | 6/1998 |
| FR | 2692773 | 12/1993 |
| GB | 2495522 | 3/2013 |
| JP | 63-005742 | 1/1988 |
| JP | 07-155297 | 6/1995 |
| JP | 10-165425 | 6/1998 |
| JP | H10-262996 | 10/1998 |
| JP | 11-192207 | 7/1999 |
| JP | 2002-125927 | 5/2002 |
| JP | 2003-325451 | 11/2003 |
| JP | 2006-102497 | 4/2006 |
| JP | 2007-152004 | 6/2007 |
| JP | 2007-296249 | 11/2007 |
| JP | 2009-268614 | 11/2009 |
| JP | 2010-104652 | 5/2010 |
| JP | 2012-016573 | 1/2012 |
| JP | 5016311 | 6/2012 |
| JP | 2014-236957 | 12/2014 |
| JP | 5661255 | 1/2015 |
| KR | 10-1782740 | 9/2017 |
| WO | WO 98/06352 | 2/1998 |
| WO | WO 98/09569 | 3/1998 |
| WO | WO 2004/002327 | 1/2004 |
| WO | WO 2005/104959 | 11/2005 |
| WO | WO 2007/063980 | 6/2007 |
| WO | WO 2008/013181 | 1/2008 |
| WO | WO 2014/020247 | 2/2014 |
| WO | WO 2014/102779 | 7/2014 |
| WO | WO 2015/028646 | 3/2015 |
| WO | WO 2015/084769 | 6/2015 |
| WO | WO 2015/107520 | 7/2015 |
| WO | WO 2016/028429 | 2/2016 |
| WO | WO 2016/028789 | 2/2016 |
| WO | WO 2016/064617 | 4/2016 |
| WO | WO 2016/068825 | 5/2016 |
| WO | WO 2016/110855 | 7/2016 |
| WO | WO 2016/113745 | 7/2016 |
| WO | WO 2016/178212 | 11/2016 |
| WO | WO 2017/125926 | 7/2017 |
| WO | WO 2017/216803 | 12/2017 |
| WO | WO 2018/047180 | 8/2018 |
| WO | WO 2019/008586 | 1/2019 |
| WO | WO 2019/021285 | 1/2019 |
| WO | WO 2019/049152 | 3/2019 |
| WO | WO 2020/144692 | 7/2020 |
| WO | WO 2022/130385 | 6/2022 |

OTHER PUBLICATIONS

Supplementary European Search Report and the European Search Opinion Dated Feb. 7, 2023 From the European Patent Office Re. Application No. 22213874.5. (11 Pages).
Official Action Dated Sep. 27, 2022 from US Patent and Trademark Office Re. U.S. Appl. No. 16/645,803. (76 pages).
Decision to Refuse A European Patent Application Dated Oct. 18, 2022 From the European Patent Office Re. Application No. 18769813.9. (15 Pages).
Official Action Dated Oct. 13, 2022 From the US Patent and Trademark Office Re. U.S. Appl. No. 16/331,974. (83 Pages).
Provision of the Minutes in Accordance With Rule 124(4) EPC Dated Oct. 12, 2022 From the European Patent Office Re. Application No. 18769813.9. (11 Pages).
Communication Pursuant to Article 94(3) EPC Dated Mar. 10, 2023 From the European Patent Office Re. Application No. 17780530.6 (3 Pages).
Restriction Official Action Dated May 17, 2022 from US Patent and Trademark Office Re. U.S. Appl. No. 16/331,974. (10 pages).
Communication Pursuant to Article 94(3) EPC Dated Jun. 22, 2023 From the European Patent Office Re. Application No. 17812894.8. (7 Pages).
Interview Summary Dated Nov. 15, 2022 from the US Patent and Trademark Office Re. U.S. Appl. No. 16/645,803. (2 pages).
Applicant-Initiated Interview Summary Dated Aug. 2, 2017 From the US Patent and Trademark Office Re. U.S. Appl. No. 15/115,196. (3 pages).
Communication Pursuant to Article 94(3) EPC Dated Oct. 5, 2021 From the European Patent Office Re. Application No. 18759184.7. (6 Pages).

(56) References Cited

OTHER PUBLICATIONS

Communication Pursuant to Article 94(3) EPC Dated Oct. 7, 2020 From the European Patent Office Re. Application No. 177805300.6. (5 Pages).
Communication Pursuant to Article 94(3) EPC Dated Aug. 10, 2017 From the European Patent Office Re. Application No. 13830124.7. (6 Pages).
Communication Pursuant to Article 94(3) EPC Dated Nov. 16, 2021 From the European Patent Office Re. Application No. 17707964.7. (4 Pages).
Communication Pursuant to Article 94(3) EPC Dated Nov. 19, 2018 From the European Patent Office Re. Application No. 13830124.7. (8 Pages).
Communication Pursuant to Article 94(3) EPC Dated Nov. 19, 2020 From the European Patent Office Re. Application No. 13830124.7. (6 Pages).
Communication Pursuant to Article 94(3) EPC Dated Jan. 29, 2021 From the European Patent Office Re. Application No. 18769813.9. (9 Pages).
Communication Pursuant to Article 94(3) EPC Dated Nov. 30, 2021 From the European Patent Office Re. Application No. 17780530.6. (4 Pages).
Communication Pursuant to Article 94(3) EPC Dated Jan. 31, 2020 From the European Patent Office Re. Application No. 17780530.6. (3 Pages).
Communication Pursuant to Rules 70(2) and 70a(2) EPC Dated Sep. 7, 2018 From the European Patent Office Re. Application No. 16789407.0. (1 Page).
Communication Relating to the Results of the Partial International Search and the Provisional Opinion Dated Jun. 14, 2017 From the International Searching Authority Re. Application No. PCT/IL2017/050072. (12 Pages).
Communication Relating to the Results of the Partial International Search Dated May 8, 2014 From the International Searching Authority Re. Application No. PCT/IL2013/051059.
Decision of Rejection Dated Jan. 14, 2020 From the Japan Patent Office Re. Application No. 2017-228103 and Its Translation Into English. (7 Pages).
English Translation Dated Nov. 30, 2021 of Ground(s) of Reason of Rejection Dated Nov. 19, 2021 From the Korean Intellectual Property Office Re. Application No. 2010-7032325. (2 Pages).
European Search Report and the European Search Opinion Dated Jan. 3, 2022 From the European Patent Office Re. Application No. 21200149.9. (10 Pages).
European Search Report and the European Search Opinion Dated Feb. 4, 2020 From the European Patent Office Re. Application 19211372.8. (10 Pages).
Final Official Action Dated Dec. 28, 2020 from the US Patent and Trademark Office Re. U.S. Appl. No. 16/634,152. (29 pages).
Ground(s) of Reason of Rejection Dated Nov. 19, 2021 From the Korean Intellectual Property Office Re. Application No. 2010-7032325. (2 Pages).
International Preliminary Report on Patentability Dated Aug. 2, 2018 From the International Bureau of WIPO Re. Application No. PCT/IL2017/050072. (10 Pages).
International Preliminary Report on Patentability Dated Feb. 6, 2020 From the International Bureau of WIPO Re. Application No. PCT/IL2018/050825. (10 Pages).
International Preliminary Report on Patentability Dated Jul. 9, 2015 From the International Bureau of WIPO Re. Application No. PCT/IL2013/051059.
International Preliminary Report on Patentability Dated Jan. 16, 2020 From the International Bureau of WIPO Re. Application No. PCT/IL2018/050731. (9 Pages).
International Preliminary Report on Patentability Dated Nov. 16, 2017 From the International Bureau of WIPO Re. Application No. PCT/IL2016/050449. (11 Pages).
International Preliminary Report on Patentability Dated Mar. 19, 2020 From the International Bureau of WIPO Re. Application No. PCT/IL2017/051014. (10 Pages).
International Preliminary Report on Patentability Dated Jul. 20, 2017 From the International Bureau of WIPO Re. Application No. PCT/IL2016/050023. (10 Pages).
International Preliminary Report on Patentability Dated Mar. 21, 2019 From the International Bureau of WIPO Re. Application No. PCT/IL2017/051015. (13 Pages).
International Preliminary Report on Patentability Dated Jul. 22, 2021 From the International Bureau of WIPO Re. Application No. PCT/IL2020/050040. (10 Pages).
International Preliminary Report on Patentability Dated Jul. 27, 2017 From the International Bureau of WIPO Re. Application No. PCT/IL2016/050058. (7 Pages).
International Search Report and the Written Opinion Dated Oct. 1, 2018 From the International Searching Authority Re. Application No. PCT/IL2018/050731. (16 Pages).
International Search Report and the Written Opinion Dated Sep. 2, 2014 From the International Searching Authority Re. Application No. PCT/IL2013/051059.
International Search Report and the Written Opinion Dated Nov. 7, 2018 From the International Searching Authority Re. Application No. PCT/IL2018/050825. (17 Pages).
International Search Report and the Written Opinion Dated Aug. 8, 2017 From the International Searching Authority Re. Application No. PCT/IL2017/050072. (17 Pages).
International Search Report and the Written Opinion Dated Dec. 11, 2018 From the International Searching Authority Re. Application No. PCT/IL2017/051014. (18 Pages).
International Search Report and the Written Opinion Dated Apr. 18, 2016 From the International Searching Authority Re. Application No. PCT/IL2016/050058.
International Search Report and the Written Opinion Dated Apr. 21, 2016 From the International Searching Authority Re. Application No. PCT/IL2016/050023.
International Search Report and the Written Opinion Dated Aug. 23, 2016 From the International Searching Authority Re. Application No. PCT/IL2016/050449.
International Search Report and the Written Opinion Dated Jul. 23, 2020 From the International Searching Authority Re. Application No. PCT/IL2020/050040. (14 Pages).
International Search Report and the Written Opinion Dated Jan. 24, 2018 From the International Searching Authority Re. Application No. PCT/IL2017/051015. (23 Pages).
Invitation to Pay Additional Fees Dated May 12, 2020 From the International Searching Authority Re. Application No. PCT/IL2020/050040. (3 Pages).
Invitation to Pay Additional Fees, Communication Relating to the Results of the Partial International Search and the Provisional Opinion Dated Apr. 8, 2022 From the International Searching Authority Re. Application No. PCT/IL2021/051499. (15 Pages).
Invitation to Pay Additional Fees, Communication Relating to the Results of the Partial International Search and the Provisional Opinion Dated Nov. 17, 2017 From the International Searching Authority Re. Application No. PCT/IL2017/051015. (17 Pages).
Notice Of Allowance Dated Aug. 9, 2018 From the US Patent and Trademark Office Re. U.S. Appl. No. 15/571,231. (17 pages).
Notice Of Allowance Dated Jul. 11, 2018 From the US Patent and Trademark Officc Re. U.S. Appl. No. 15/115,196. (8 pages).
Notice Of Allowance Dated May 12, 2016 From the US Patent and Trademark Office Re. U.S. Appl. No. 14/655,286.
Notice of Allowance Dated Jul. 13, 2021 from the US Patent and Trademark Office Re. U.S. Appl. No. 16/227,995. (7 pages).
Notice of Allowance Dated Nov. 30, 2020 from the US Patent and Trademark Office Re. U.S. Appl. No. 16/071,058. (10 pages).
Notice of Reasons for Rejection Dated May 7, 2019 From the Japan Patent Office Re. Application No. 2017-228103 and Its Translation Into English. (8 Pages).
Notice of Reasons for Rejection Dated Jul. 11, 2017 From the Japan Patent Office Re. Application No. 2015-548888 and Its Translation Into English. (5 Pages).
Notice of Reasons for Rejection Dated Feb. 14, 2017 From the Japan Patent Office Re. Application No. 2015-548888 and Its Translation Into English. (10 Pages).

(56) References Cited

OTHER PUBLICATIONS

Notice of Reasons for Rejection Dated Sep. 25, 2018 From the Japan Patent Office Re. Application No. 2017-228103 and Its Translation Into English. (15 Pages).
Notice Requesting Submission of Opinion Dated Feb. 3, 2021 From the Korean Intellectual Property Office Re. Application No. 10-2020-7032325 and Its Translation Into English. (14 Pages).
Notice Requesting Submission of Opinion Dated Jan. 21, 2020 From the Korean Intellectual Property Office Re. Application No. 10-2019-7034814. (3 Pages).
Notice Requesting Submission of Opinion Dated Apr. 26, 2019 From the Korean Intellectual Property Office Re. Application No. 10-2015-7020305. (4 Pages).
Notification of Office Action and Search Report Dated Jan. 5, 2017 From the State Intellectual Property Office of the People's Republic of China Re. Application No. 201380071840.0. (7 Pages).
Notification of Office Action Dated Apr. 15, 2016 From the State Intellectual Property Office of the People's Republic of China Re. Application No. 201380071840.0.
Office Action Dated Aug. 6, 2019 From the Israel Patent Office Re. Application No. 264237 and Its Translation Into English. (6 Pages).
Official Action Dated Sep. 3, 2021 from the US Patent and Trademark Office Re. U.S. Appl. No. 16/634,152. (43 pages).
Official Action Dated Nov. 4, 2020 From the US Patent and Trademark Office Re. U.S. Appl. No. 15/274,756. (19 Pages).
Official Action Dated Mar. 9, 2017 From the US Patent and Trademark Office Re. U.S. Appl. No. 15/115,196. (26 pages).
Official Action Dated Jun. 12, 2020 from the US Patent and Trademark Office Re. U.S. Appl. No. 16/634,152. (41 pages).
Official Action Dated Dec. 13, 2017 From the US Patent and Trademark Office Re. U.S. Appl. No. 15/115,196. (26 pages).
Official Action Dated Jun. 13, 2019 From the US Patent and Trademark Office Re. U.S. Appl. No. 15/274,756. (39 pages).
Official Action Dated May 15, 2020 from the US Patent and Trademark Office Re. U.S. Appl. No. 16/071,058. (31 pages).
Official Action Dated Feb. 19, 2021 From the US Patent and Trademark Office Re. U.S. Appl. No. 16/227,995. (27 Pages).
Official Action Dated Sep. 28, 2016 From the US Patent and Trademark Office Re. U.S. Appl. No. 15/115,196. (19 pages).
Official Action Dated Apr. 3, 2020 from the US Patent and Trademark Office Re. U.S. Appl. No. 16/199,954. (31 pages).
Requisition by the Examiner Dated Oct. 4, 2019 From the Innovation, Science and Economic Development Canada, Canadian Intellectual Property Office Re. Application No. 2,896,210. (3 Pages).
Restriction Official Action Dated May 3, 2022 from US Patent and Trademark Office Re. U.S. Appl. No. 16/645,803. (7 pages).
Restriction Official Action Dated Nov. 14, 2019 From the US Patent and Trademark Office Re. U.S. Appl. No. 16/199,954. (6 pages).
Restriction Official Action Dated Sep. 26, 2018 From the US Patent and Trademark Office Re. U.S. Appl. No. 15/274,756. (10 Pages).
Summons to Attend Oral Proceedings Pursuant to Rule 115(1) EPC Dated Mar. 18, 2022 From the European Patent Office Re. Application No. 18769813.9. (9 Pages).
Summons to Attend Oral Proceedings Pursuant to Rule 115(1) EPC Dated Mar. 19, 2020 From the European Patent Office Re. Application No. 13830124.7. (13 Pages).
Summons to Attend Oral Proceedings Pursuant to Rule 115(1) EPC Dated Mar. 19, 2021 From the European Patent Office Re. Application No. 17780530.6. (7 Pages).
Summons to Attend Oral Proceedings Pursuant to Rule 115(1) EPC Dated Apr. 20, 2021 From the European Patent Office Re. Application No. 17780530.6. (2 Pages).
Supplementary European Search Report and the European Search Opinion Dated Feb. 19, 2021 From the European Patent Office Re. Application No. 18837606.5. (7 Pages).
Supplementary European Search Report and the European Search Opinion Dated Aug. 21, 2018 From the European Patent Office Re. Application No. 16789407.0. (6 Pages).
Translation Dated Feb. 2, 2020 of Notice Requesting Submission of Opinion Dated Jan. 21, 2020 From the Korean Intellectual Property Office Re. Application No. 10-2019-7034814. (3 Pages).
Translation Dated May 9, 2019 of Notice Requesting Submission of Opinion Dated Apr. 26, 2019 From the Korean Intellectual Property Office Re. Application No. 10-2015-7020305. (4 Pages).
Translation Dated Nov. 30, 2021 of Ground(s) of Reason of Rejection Dated Nov. 19, 2021 From the Korean Intellectual Property Office Re. Application No. 2010-7032325. (2 Pages).
Translation of Notification of Apr. 15, 2016 From the State Intellectual Property Office of the People's Republic of China Re. Application No. 201380071840.0.
Translation of Notification of Office Action Dated Jan. 5, 2017 From the State Intellectual Property Office of the People's Republic of China Re. Application No. 201380071840.0. (4 Pages).
Bouguet et al. "3D Photography Using Shadows in Dual-Space Geometry", The International Journal of Computer Vision, 35(2): 129-149, Nov./Dec. 1999.
Fluegge et al. "Precision of Intraoral Digital Dental Impressions With iTero and Extraoral Digitization With the iTero and A Model Scanner", American Journal of Orthodontics and Dentofacial Orthopedics, 144(3): 471-478, Sep. 2013.
Geng "Structured-Light 3D Surface Imaging: A Tutorial", Advances in Optics and Photonics, 3: 128-160, 2011.
Goshtasby et al. "A System for Digital Reconstruction of Gypsum Dental Casts", IEEE Transactions On Medical Imaging, 16(5): , Oct. 1997.
Logozzo et al. "Recent Advances in Dental Optics—Part I: 3D Intraoral Scanners for Restorative Dentistry", Optics and Lasers in Engineering, 54: 203-221, Mar. 2014.
Maintz et al. "A Survey of Medical Image Registration", Medical Image Analysis, 2(1): 1-36, Mar. 1998.
Medeiros et al. "Coded Structred Light for 3D-Photography: An Overview", IEEE-RITA, (Latin-American Learning Technologies Journal), IV(2): 109-124, Jul. 1999.
OmniVision "OVM6946 400×400. Compact, Cost-Effective Wafer-Level Camera Module for Single-Use Endoscopes", OmniVision, Product Brief, 2 P., Aug. 10, 2016.
Paperno et al. "A New Method for Magnetic Position and Orientation Tracking", IEEE Transactions on Magnetics, XP011033696, 37(4): 1938-1940, Jul. 2001.
Salvi et al. "Pattern Codification Strategies in Structured Light Systems", Pattern Recognition, 37(4): 827-849, 2004.
Savarese et al. "3D Reconstruction by Shadow Carving: Theory and Practical Evaluation", International Journal of Computer Vision, 71(3): 305-336, Published Online Jun. 1, 2006.
Toshiba "IK-CT2: 0.7×0.7 mm, 220×220, CMOS", Toshiba Information Systems, Product Sheet, 1 P., Dec. 2016.
Notice of Allowance Dated Mar. 7, 2023 from the US Patent and Trademark Office Re. U.S. Appl. No. 16/331,974. (14 pages).
Final Official Action Dated Apr. 12, 2021 From the US Patent and Trademark Office Re. U.S. Appl. No. 16/310,435. (19 Pages).
International Preliminary Report on Patentability Dated Dec. 27, 2018 From the International Bureau of WIPO Re. Application No. PCT/IL2017/050674. (9 Pages).
International Search Report and the Written Opinion Dated Sep. 18, 2017 From the International Searching Authority Re. Application No. PCT/IL2017/050674. (12 Pages).
Notice of Allowance Dated Dec. 15, 2021 from US Patent and Trademark Office Re. U.S. Appl. No. 16/310,435. (6 pages).
Official Action Dated Aug. 19, 2021 From the US Patent and Trademark Office Re. U.S. Appl. No. 16/310,435. (7 Pages).
Official Action Dated Oct. 27, 2020 From the US Patent and Trademark Office Re. U.S. Appl. No. 16/310,435. (11 Pages).
Supplementary European Search Report and the European Search Opinion Dated Jan. 21, 2020 From the European Patent Office Re. Application No. 17812894.8. (10 Pages).
Official Action Dated Aug. 23, 2023 from the US Patent and Trademark Office Re. U.S. Appl. No. 16/645,803. (18 pages).
International Preliminary Report on Patentability Dated Jun. 29, 2023 From the International Bureau of WIPO Re. Application No. PCT/IL2021/051499. (15 Pages).

(56) References Cited

OTHER PUBLICATIONS

Official Action Dated May 23, 2024 from the US Patent and Trademark Office Re. U.S. Appl. No. 16/645,803. (5 pages).

* cited by examiner

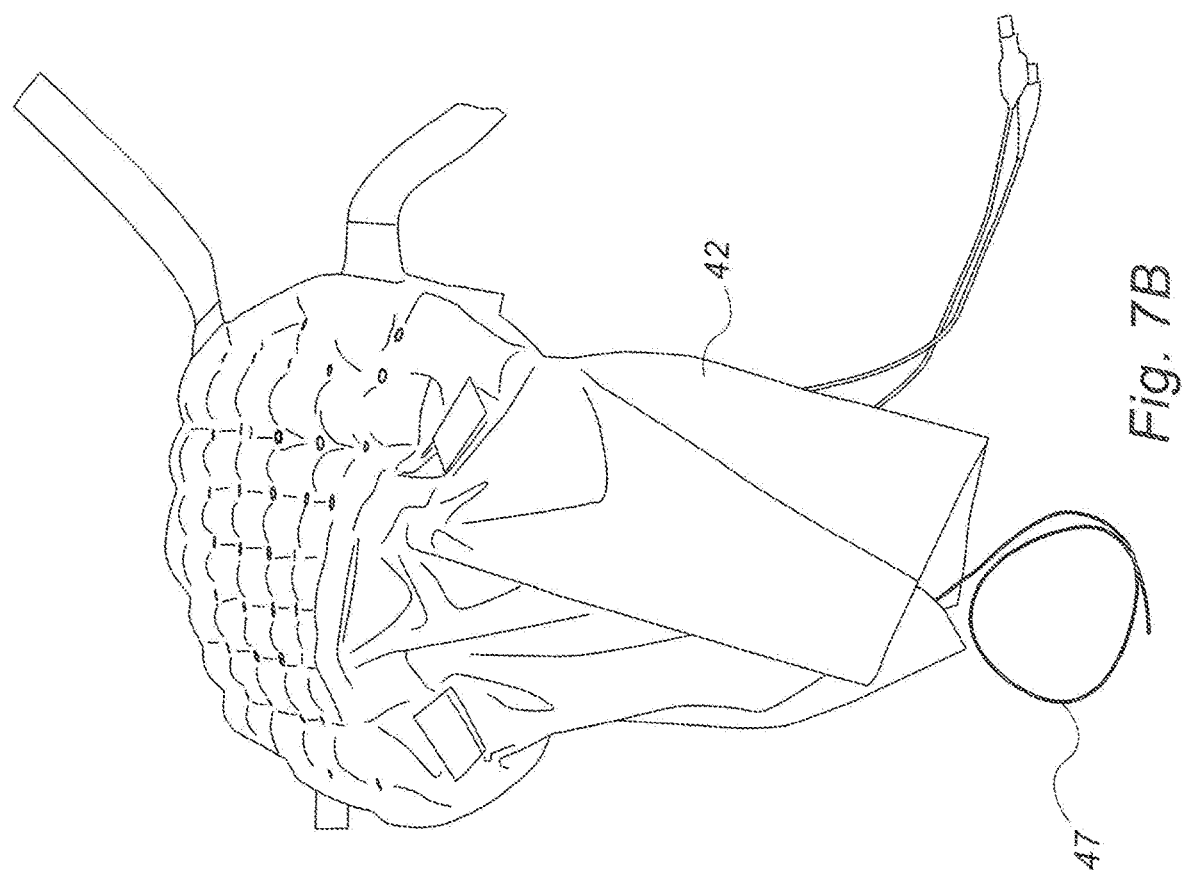
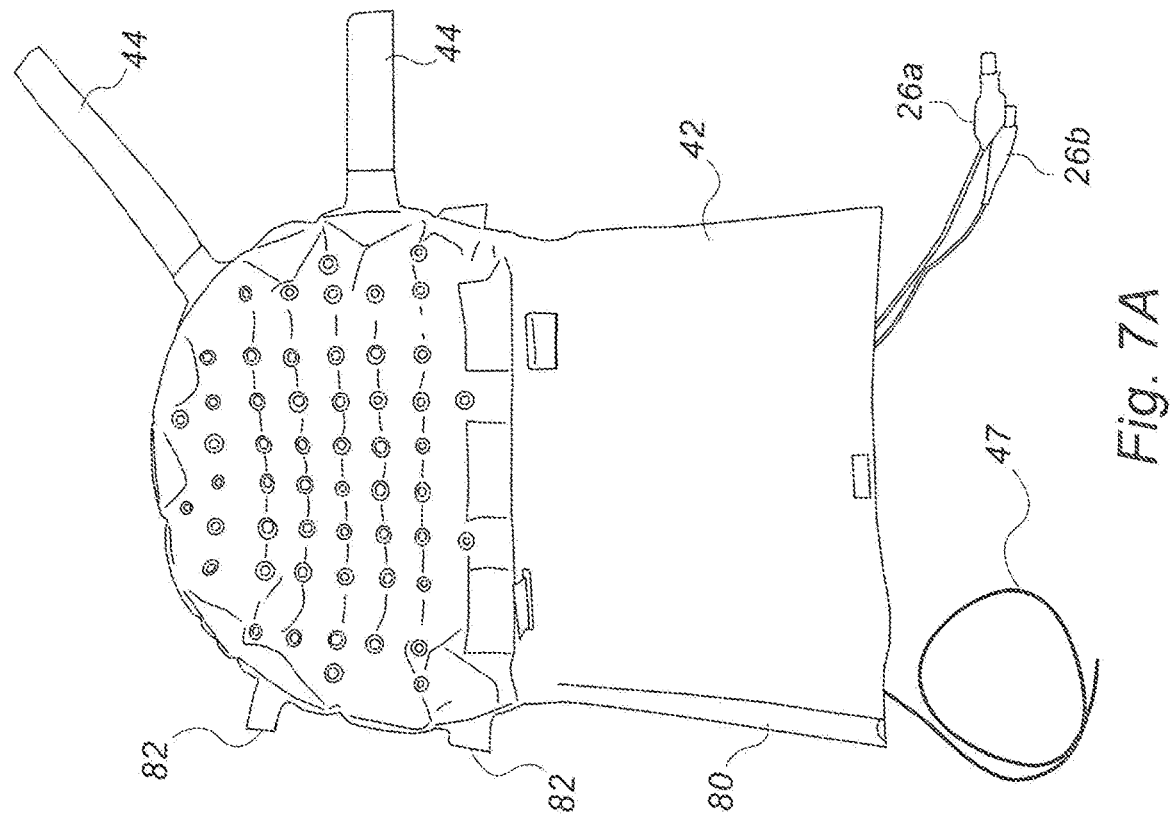

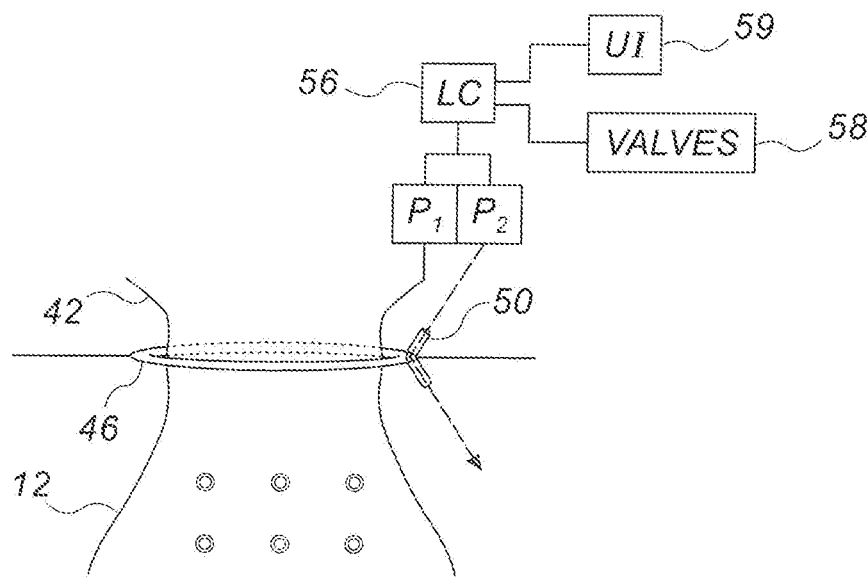
Fig. 13A
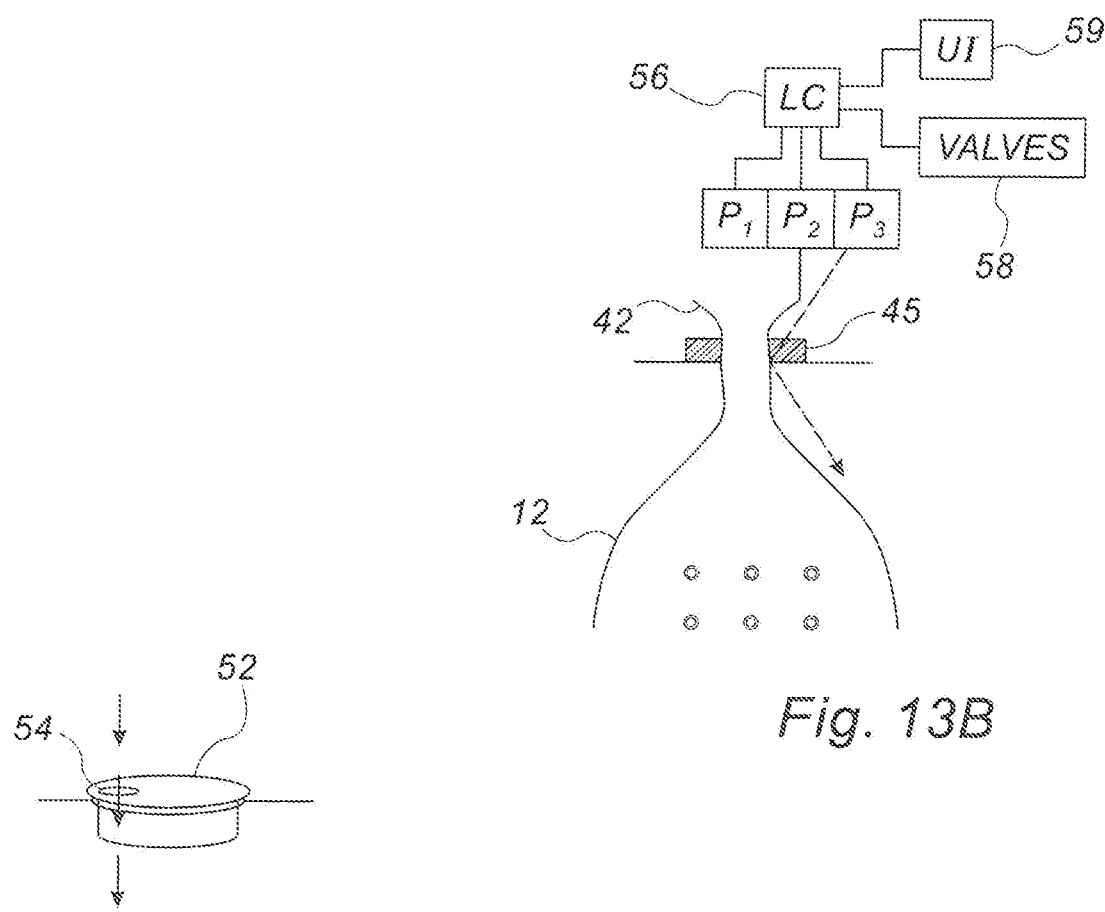
Fig. 13B
Fig. 13C

TISSUE CONTAINMENT DEVICE FOR USE IN SURGICAL PROCEDURES

RELATED APPLICATIONS

This application is a continuation of U.S. patent application Ser. No. 16/310,435 Filed on Dec. 16, 2018, which is a National Phase of PCT Patent Application No. PCT/IL2017/050674 having International Filing Date of Jun. 18, 2017, which claims the benefit of priority under 35 USC § 119(e) of U.S. Provisional Patent Application No. 62/350,745 filed on Jun. 16, 2016. The contents of the above applications are all incorporated by reference as if fully set forth herein in their entirety.

FIELD AND BACKGROUND OF THE INVENTION

The present invention relates to surgical devices and, in particular, it concerns a tissue containment device for isolating tissue from surrounding tissue during a surgical procedure to remove the tissue, and corresponding systems and methods.

During the performance of various gynecological procedures, such as myomectomy and hysterectomy, via an access opening which is smaller than the size of the uterus to be removed, a tissue reduction (or morcellation) process is required in order to reduce dimensions of the tissue to facilitate removal. Such processes raise concerns regarding the potential dissemination of tissue that is suspected of including cancerous cells, with an associated risk of seeding cancer growth at other locations within the body.

In an attempt to mitigate this risk, it has been proposed to introduce the tissue into an intra-body containment bag within which the tissue reduction process is performed. There remains however a significant risk of perforation of the bag by the various tools used during the procedure. Such perforation may go undetected, and may still allow leakage of cancerous cells into the abdominal cavity.

SUMMARY OF THE INVENTION

The present invention is a tissue containment device for isolating tissue from surrounding tissue during a surgical procedure to remove the tissue, and corresponding systems and methods employing the device.

According to the teachings of an embodiment of the present invention there is provided, a tissue containment device for isolating tissue from surrounding tissue during a surgical procedure to remove the tissue, the device comprising: (a) a bag comprising one or more walls, defining a containment compartment and an opening for accessing the containment compartment, wherein the one or more walls are formed from at least two layers defining at least one inflatable volume therebetween; and (b) at least one inflation port in fluid connection with the at least one inflatable volume for introducing and removing a fluid to and from the at least one inflatable volume, wherein the at least two layers are interconnected at spaced-apart connection regions, the spaced-apart connection regions being configured such that, when a fluid is introduced to the at least one inflatable volume, regions of the at least two layers between the connection regions form wall cavity regions substantially surrounding an internal volume of the containment compartment.

According to a further feature of an embodiment of the present invention, the wall cavity regions extend over at least 85% of an inward facing surface of the at least one wall facing the internal volume as projected to a centroid of the internal volume.

According to a further feature of an embodiment of the present invention, the wall cavity regions form a plurality of adjacent bulges in proximity to each other such that an instrument having a width of at least 8 mm cannot reach the connection regions without first contacting the bulges.

According to a further feature of an embodiment of the present invention, the at least two layers are implemented as initially flat sheets of material that are selectively interconnected at the connection regions.

According to a further feature of an embodiment of the present invention, an outer layer of the at least two layers is implemented as a layer having an increased resistance to flexing compared to an inner layer of the at least two layers.

According to a further feature of an embodiment of the present invention, an outer layer of the at least two layers differs from an inner layer of the at least two layers in at least one property selected from the group consisting of: shear strength, burst limit and puncture resistance.

According to a further feature of an embodiment of the present invention, the at least two layers are implemented as three layers of material, and wherein spaced apart connection regions between a first of the layers and a second of the layers are interspaced between spaced apart connection regions between the second of the layers and a third of the layers.

According to a further feature of an embodiment of the present invention, an inward-facing layer of the at least two layers is implemented with preformed inflatable pockets between the connection regions.

According to a further feature of an embodiment of the present invention, the bag assumes a compact state in which a first region of the at least one wall is adjacent to a second region of the at least one wall, and wherein the spaced-apart connection regions define elongated inflatable deployment cavities extending within the first and second regions such that, on inflation of the at least one inflatable volume, the inflatable deployment cavities press against each other so as to tend to force apart the first and second regions, thereby opening up the internal volume of the containment compartment.

According to a further feature of an embodiment of the present invention, the at least one wall is configured to form at least two of the inflatable volumes, the at least two inflatable volumes being independently inflatable.

According to a further feature of an embodiment of the present invention, the spaced-apart connection regions are deployed so as to define elongated inflatable boundary cavities extending so as to circumscribe a majority of the opening such that, on inflation of the at least one inflatable volume, the inflatable boundary cavities tend to open the opening.

According to a further feature of an embodiment of the present invention, the spaced-apart connection regions are deployed such that, on inflation of the at least one inflatable volume, at least part of the at least one wall presents an array of inflated bulges in facing relation to the containment volume, and further comprising printed markings disposed within a central region of a plurality of the bulges.

According to a further feature of an embodiment of the present invention, the at least one wall comprises two walls interconnected at a peripheral seal such that the bag is formed from at least four of the layers in overlying relation.

According to a further feature of an embodiment of the present invention, the bag further comprises at least one loop element deployed on an external surface of the bag, the loop element being located to facilitate rolling of the bag by insertion of an instrument through the at least one loop element and rotation of the instrument.

According to a further feature of an embodiment of the present invention, there is also provided a pressure indicator in fluid interconnection with the inflatable volume, the pressure indicator being configured to generate a visible and/or audible indication when a pressure within the inflatable volume decreases or falls below a reference pressure value.

According to a further feature of an embodiment of the present invention, the bag further comprises at least one instrument insertion branch implemented as a flexible access tube communicating with the containment compartment and allowing instrument access via an incision in a direction angularly spaced from the opening of the bag.

According to a further feature of an embodiment of the present invention, the instrument insertion branch is formed by an extension of at least one of the layers from each of two regions of the at least one wall, the extensions being interconnected to form a collapsible tube.

According to a further feature of an embodiment of the present invention, the at least two layers are manufactured from a thermoplastic material.

There is also provided according to the teachings of an embodiment of the present invention, a system for implementing a surgical procedure to remove tissue from a body, the system comprising: (a) the aforementioned device; and (b) a heat sealing device configured for performing a heat sealing process on the instrument insertion branch so as to prevent leakage of cells from the instrument insertion branch on introduction of the instrument insertion branch into the body.

There is also provided according to the teachings of an embodiment of the present invention, a system for implementing a surgical procedure to remove tissue from a body, the system comprising: (a) the aforementioned device; (b) a source of pressurized fluid for connection to the at least one inflation port; and (c) a tissue reducing device for insertion through the opening for reducing a dimension of tissue located within the containment compartment.

According to a further feature of an embodiment of the present invention, there is also provided a pressure monitoring system comprising: (a) a pressure sensor deployed for sensing a pressure within the at least one inflatable volume; and (b) logic circuitry in communication with the pressure sensor and configured to monitor variations in the pressure within the at least one inflatable volume to determine whether the variations are indicative of a malfunction condition of the bag.

According to a further feature of an embodiment of the present invention, the logic circuitry is further configured to generate an audible and/or visible indication on identification of a malfunction condition of the bag.

According to a further feature of an embodiment of the present invention, the logic circuitry is further configured to determine if a layer of the bag has been breached and, in response to such breaching, to generate an output for initiating a corrective action, the corrective action including increasing a pressure supplied to the inflatable volume.

According to a further feature of an embodiment of the present invention, the bag further comprises an access sleeve sealingly connected to the opening and defining a sealed access channel for performing a tissue reduction process on tissue within the containment compartment.

According to a further feature of an embodiment of the present invention, there is also provided an abdominal cavity insufflation port and an associated flow channel configured for providing insufflation pressure to an abdominal cavity external to the access sleeve.

According to a further feature of an embodiment of the present invention, a pressure monitoring system comprising: (a) a first pressure sensor deployed for sensing a pressure within the at least one inflatable volume; (b) a second pressure sensor configured for deployment to sense abdominal cavity pressure exterior to the bag; and (c) logic circuitry in communication with the first and second pressure sensors, and configured to monitor variations in the pressure within the at least one inflatable volume relative to the pressure exterior to the bag, and to determine whether the variations are indicative of a malfunction condition of the bag.

According to a further feature of an embodiment of the present invention, the logic circuitry is further configured to generate an audible and/or visible indication on identification of a malfunction condition of the bag.

According to a further feature of an embodiment of the present invention, the logic circuitry is further configured to determine if a layer of the bag has been breached and, in response to such breaching, to generate an output for initiating a corrective action, the corrective action including increasing a pressure supplied to the abdominal cavity volume exterior to the bag.

According to a further feature of an embodiment of the present invention, there is also provided a third pressure sensor deployed for sensing a pressure within the containment compartment, the logic circuitry further being in communication with the third pressure sensor.

There is also provided according to the teachings of an embodiment of the present invention, a method for surgical removal of tissue from a body, the method comprising the steps of: (a) introducing the device of claim 24 into the body through an incision or body orifice in a compact, uninflated state; (b) inflating the inflatable volume with a fluid so as to deploy the bag within the body; (c) inserting into the bag the tissue to be removed from the body; (d) extending the access sleeve out through the incision or body orifice; (e) performing via the access sleeve reduction and removal of the tissue; (f) deflating the inflatable volume while maintaining part of the access sleeve extending out through the incision or body orifice; and (g) removing the device via the incision or body orifice.

According to a further feature of an embodiment of the present invention, insertion of the device is performed via a laparoscopic incision.

According to a further feature of an embodiment of the present invention, the inflation is performed using saline solution.

According to a further feature of an embodiment of the present invention, the bag further comprises at least one instrument insertion branch implemented as a flexible access tube communicating with the containment compartment, the method further comprising extending the at least one instrument insertion branch out through an incision or body orifice.

According to a further feature of an embodiment of the present invention, an instrument is inserted through the at least one instrument insertion branch.

According to a further feature of an embodiment of the present invention, the at least one instrument insertion branch is heat sealed prior to reintroduction of the instrument insertion branch into the body.

According to a further feature of an embodiment of the present invention, the device is formed with at least one loop element, the method further comprising inserting at least one instrument through the at least one loop element, and rolling at least part of the device around the instrument.

According to a further feature of an embodiment of the present invention, a pressure is sensed within the at least one inflatable volume and variations in the pressure are monitored to determine whether variations in the pressure are indicative of a malfunction condition of the bag.

According to a further feature of an embodiment of the present invention, an abdominal cavity exterior to the bag is insufflated and a pressure within the abdominal cavity exterior to the bag is sensed.

According to a further feature of an embodiment of the present invention, the containment compartment of the bag is inflated and a pressure within the containment compartment of the bag is sensed.

According to a further feature of an embodiment of the present invention, it is determined whether a layer of the bag has been breached and, in response to such breaching, a corrective action is initiated, the corrective action including introducing a fluid into the inflatable volume and/or into the abdominal cavity exterior to the bag.

BRIEF DESCRIPTION OF THE SEVERAL VIEWS OF THE DRAWING(S)

The invention is herein described, by way of example only, with reference to the accompanying drawings, wherein:

FIGS. 7A and 7B are isometric views of the device of FIG. 1A after extending of a sealed access sleeve, the device being shown in uninflated and inflated states, respectively;

FIGS. 13A and 13B are schematic representations of arrangements for applying pressure and monitoring pressure in the cases of FIGS. 11 and 12, respectively;

FIG. 13C illustrates schematically a further option for insufflation of the abdominal cavity via a separate incision;

DESCRIPTION OF SPECIFIC EMBODIMENTS OF THE INVENTION

Figure 1A:
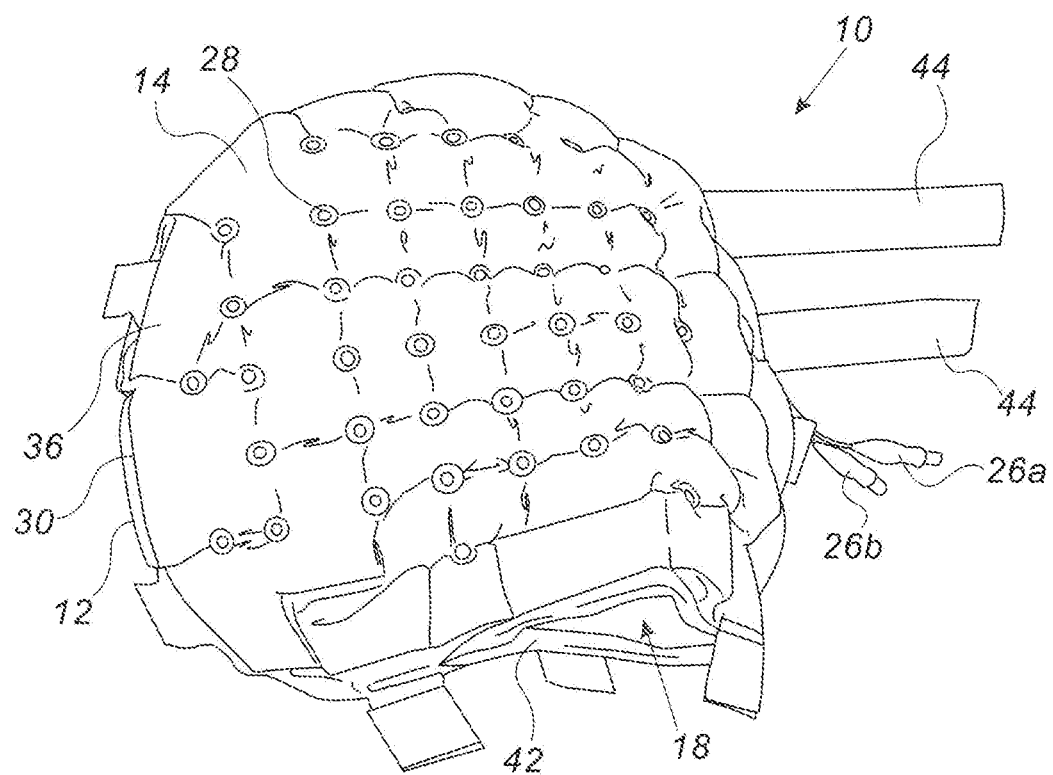
FIGS. 1A and 1B are isometric views of a tissue containment device, constructed and operative according to an embodiment of the present invention, for isolating tissue from surrounding tissue during a surgical procedure to remove the tissue, the device being shown in an inflated state.
Figure 1B:
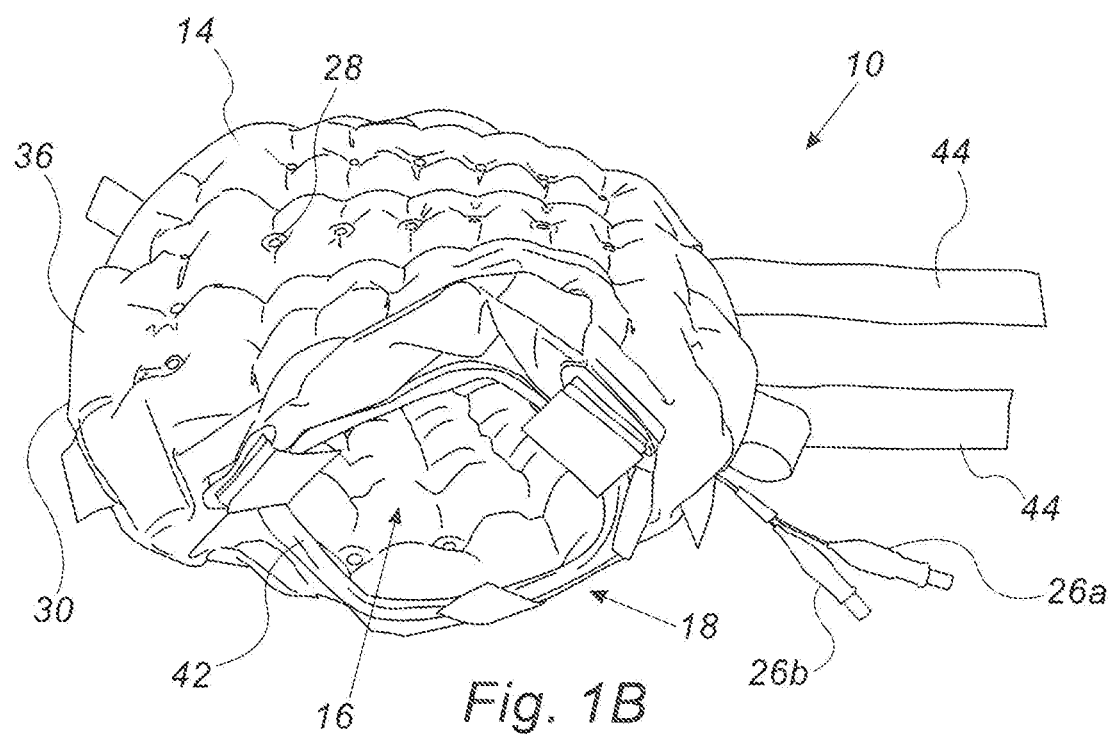

The present invention is a tissue containment device for isolating tissue from surrounding tissue during a surgical procedure to remove the tissue, and corresponding systems and methods employing the device.

The principles and operation of devices, systems and methods according to the present invention may be better understood with reference to the drawings and the accompanying description.

Referring now to the drawings, FIGS. 1-20 illustrate the structure and operation of a tissue containment device, generally designated 10, constructed and operative according to the teachings of an embodiment of the present invention, for isolating tissue from surrounding tissue during a surgical procedure to remove the tissue. In general terms, device 10 has a bag 12 formed by one or more walls 14 defining a containment compartment 16 and an opening 18 for accessing the containment compartment. Each wall 14 is formed from at least two layers including an inner layer 20 facing the containment compartment and an outer layer 22 facing outwards from bag 12. The layers define between them one or more inflatable volumes 24 in fluid connection with a corresponding one or more inflation ports 26a, 26b for introducing and removing a fluid to and from the at least one inflatable volume.

It is a particular feature of certain preferred implementations of the present invention that the at least two layers 20 and 22 are interconnected at spaced-apart connection regions 28 that are arranged such that, when a fluid is introduced into the inflatable volumes 24, regions of the at least two layers between the connection regions form wall cavity regions substantially surrounding an internal volume of the containment compartment.

It will be appreciated that the provision of inflated wall cavity regions substantially surrounding the internal volume of the containment compartment provides profound advantages regarding the potential risks of disseminating tissue that is suspected to include cancerous cells during a tissue removal procedure. Specifically, by providing a cavity wall structure in which at least two layers are separated by a fluid-filled cavity, the risks of leakage from the bag are greatly reduced, since any minor puncture will typically penetrate one layer without reaching the second layer. Furthermore, the presence of a fluid-filled volumes maintained at a pressure elevated above atmospheric pressure surrounding the internal volume facilitates immediate detection of any puncture event through detection of loss of pressure. These and other features of preferred embodiments of the present will be described further below.

The present invention is applicable to a wide range of laparoscopic and open surgery procedures, whether performed through one or more external incision and/or via a body orifice. Examples include, but are not limited to, various gynecological procedures, such as myomectomy and hysterectomy.

Where reference is made to "tissue reduction", this refers to a process through which at least one dimension of a piece of tissue is reduced in order to facilitate removal of the tissue from the body. Tissue reduction thus defined includes a wide range of techniques, including power morcellation and various sectioning processes, for example, manual morcellation during which a piece of tissue may be converted into an elongated rope of tissue, or into a number of separate pieces. A tissue reduction tool may employ one or more blades, or may use RF or other energy applicators to convert the form of the tissue.

Where reference is made herein in the description to inflation using a fluid, the term is used generically to refer to options of inflation by gas or by liquid. Gases suitable for inflation of device 10 include all biocompatible gases such as those that are typically used for insufflation of the abdominal cavity during laparoscopic procedures, including but not limited to carbon dioxide, nitrous oxide and helium. Liquids suitable for inflation of device 10 include all biocompatible liquids, including but not limited to isotonic saline solution, optionally with a marker or dye to facilitate visual detection of any puncture, or optionally a liquid used to enhance transparency of walls 14.

The term "wall cavity region" is used herein in the description and claims to refer to any regions of wall in which two layers of the wall are separated by fluid-filled cavity, thereby requiring penetration of two spaced-apart layers before a leakage path through the wall would result.

As mentioned, it is a particular feature of one aspect of the present invention that the wall cavity regions formed by inflatable volumes 24 when inflated substantially surround an internal volume of the containment compartment. In this context, "substantially surround" is used to refer to an arrangement in which the inflatable volumes are sufficiently closely packed and have sufficiently small spaces between them that any puncturing of an inner layer of the bag by a tissue reduction tool, such as a power morcellator, or by any other instrument used during the procedure is likely to result in breaching of one of the inflatable volumes, and will thus cause pressure loss to the inflatable volume. "Surrounding" in this context refers to the walls of the bag 12 which define the containment compartment, but excludes the area of opening 18. There are a number of different structural features and options which may contribute to this property, as will be described below.

Firstly, the spaced apart connection regions 28 are preferably laid out in a pattern in which each connection region is relatively small or narrow. In most cases, the connection regions have at least one dimension which is less than 8 mm, preferably no more than 5 mm, and typically in the range of 2-3 mm. The same dimensional limitations are preferably also true for any continuous seal lines separating between inflatable volumes (discussed further below) that are in facing relation to the containment compartment. (Seal lines at which two regions of wall meet and turn outwards from the bag, such as those at an outer seam 30 of the illustrated embodiment, may be larger than the above dimensions, since the width of the seam is not exposed to the containment compartment.) The connection regions 28 and any seal lines passing across the inward-facing surfaces of the walls preferably have a total area of not more than 20% of the internal surface area of the bag prior to inflation, and more preferably not more than 10%. In certain cases, particularly where the spaced apart connection regions 28 are implemented primarily as a pattern of isolated "dot" regions, the total area of these regions is typically about 5% or less.

Figure 2A:
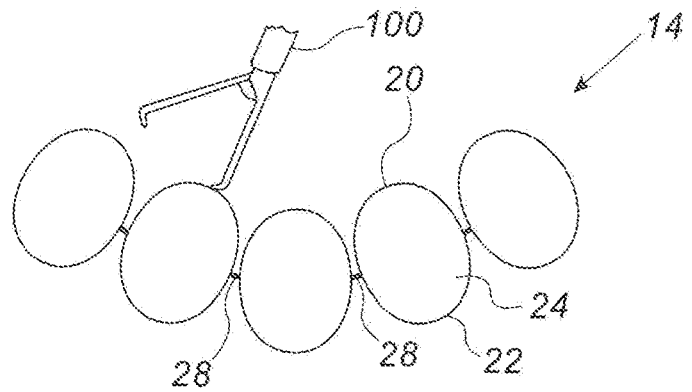
FIGS. 2A and 2B are schematic partial cross-sectional views taken through a wall of the device of FIG. 1A illustrating two versions of a wall structure.
Figure 2B:
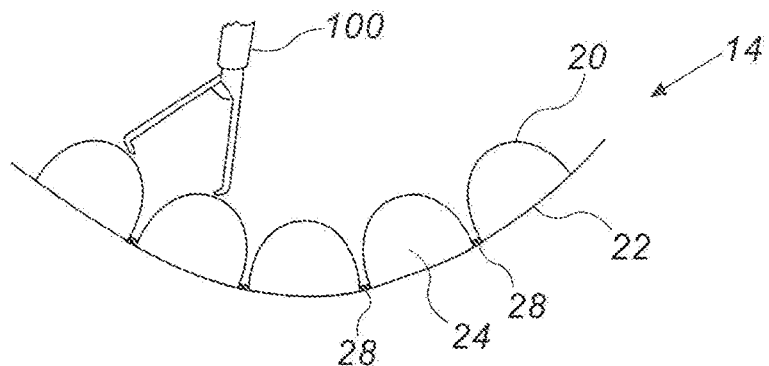
Figure 3:
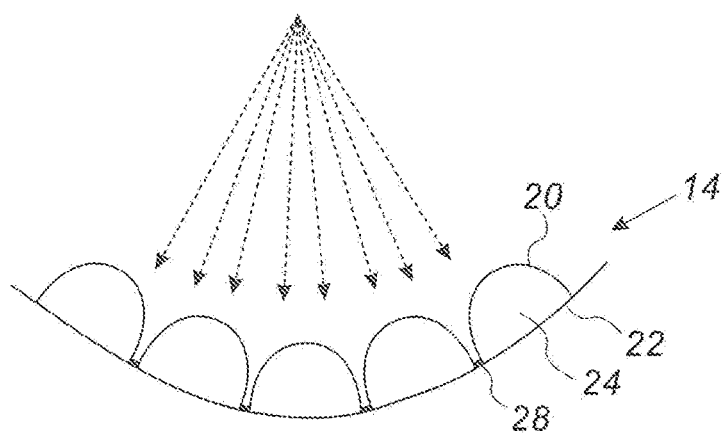
FIG. 3 is a schematic view similar to FIG. 2B illustrating a projection from a centroid of a volume within a containment compartment of the device towards the wall.

Inaccessibility of the connection regions 28 for accidental perforation is preferably further enhanced by the geometrical form assumed by inflatable volumes 24 when inflated. Firstly, the inflatable volumes of certain embodiments form inward bulges of inner layer 20. Because of these inward bulges, the inflated regions are typically encountered first by any instrument which is inadvertently advanced towards the wall. Furthermore, the adjacent peripheral edges of the bulges typically form a crevice at connection regions 28, which may in some cases have an acute angle of convergence, as illustrated in FIGS. 2A and 2B. This crevice configuration further reduces the probability of an instrument causing puncture in the region of connection without impinging on the inflatable volumes, since such selective puncture would only be likely to occur in the event of an instrument of particular dimensions which approaches the crevice within a particular range of angles of approach, and with a specific instrument orientation that presents a sufficiently narrow profile.

The proximity of the adjacent bulges adjacent to each region of connection is preferably sufficiently small that an instrument having a width of at least 8 mm, and most preferably even 5 mm, or even 3 mm, cannot reach the connection regions without first contacting the bulges.

Another way to express the property that the wall cavity regions formed by inflatable volumes 24 when inflated substantially surround an internal volume of the containment compartment is by considering a projection of the wall surface towards a centroid of the internal volume of the containment compartment. This is illustrated in the partial view of FIG. 3, where dashed lines extend between the centroid of the internal volume of the inflated bag and the wall. According to this definition, the wall cavity regions preferably extend over at least 85%, more preferably at least 90%, and in certain cases at least 95% or even at least 97%, of the inward facing surface of the walls facing the internal volume as projected towards a centroid of the internal volume. In alternative terms, this may be considered the proportion of the solid angle subtended at the centroid by the wall cavity regions compared to that of the wall as a whole, not including the opening.

The wall structure of bag 12 may be implemented in many ways, and generate many variant structures which exhibit properties as described above. According to one particularly preferred subset of implementations, the layers 20, 22 of the walls are formed primarily as layers of biocompatible thermoplastic material which are selectively welded together by some combination of heat and pressure to form connection regions 28. In one example, the structure can be formed from two bags, which may themselves be seamless, placed one inside the other and then interconnected at an arrangement of spaced apart connection regions 28, thereby forming a bag that is essentially a single-wall structure with a layered wall structure. A similar approach can be taken to a three-layer wall structure, as discussed below.

In an alternative subset of implementations, separate regions of the wall or walls are connected to each other, also typically by a welding process, to form a seam of bag 12. This may be achieved by taking a two-layer wall and folding it over to double on itself followed by a heat/pressure welding process, or by stacking two separate layered walls and performing a heat/pressure welding process. In certain cases, the bag typically exhibits a flat pouch-like form when uninflated, which opens into a three dimensional open pouch on inflation. It should be noted that the above examples, while considered particularly advantageous, are not limiting, and many other ways of forming an appropriate layered-wall bag structure also fall within the scope of the present invention.

Examples of possible structures of the layered wall, shown in an inflated state, are illustrated schematically in FIGS. 2A, 2B, 4A and 4B. In the case of FIG. 2A, two similar layers 20, 22, typically initially in the form of flat sheets, are interconnected at connection regions 28, thereby defining inflatable volumes 24 which, when inflated form wall cavities between the layers extending between the connection regions. In this case, the two layers typically bulge outwards from the local midline of the wall roughly symmetrically to the inside and outside of the bag, although the inward bulges are typically closer to each other due to an overall concave profile of the bag wall.

In some cases, it may be preferred to generate asymmetric wall cavity regions where the external layer 22 is relatively smoother than the internal layer 20, thereby minimizing the risk of applying localized pressure on adjacent organs within the abdominal cavity. An example of such a structure is shown in FIG. 2B. This structure may be achieved by defining a preferential direction of inflation of the cavities, by pre-shaping layer 20 to have pre-formed inflatable cavities and/or by forming outer layer 22 with increased resistance to flexing compared to inner layer 20. An increased resistance to flexing may be generated by using an increased thickness layer and/or by use of different materials, or reinforced materials, for the different layers. Pre-shaping of a layer with pre-formed inflatable cavities can be achieved by various polymer production techniques, such as flow-forming or suction-forming, all as is known in the art.

It will be noted that the ability to form the bag wall from a number of layers having different properties can be used to advantage in other ways. For example, in some cases, it may be advantageous to provide outer layer 22 and inner layer 20 with different properties for at least one of the properties: shear strength, burst limit and puncture resistance. For example, in order to facilitate compact insertion and removal of the device, it may be preferable to combine one layer which provides the requisite physical properties for burst limit, puncture resistance etc. while the remaining layer or layers are formed from relatively thinner material which are more easily compacted by rolling or the like when deflated.

In certain cases, it may be advantageous to employ more than two layers in the wall of the device. In one example, illustrated in FIG. 4A, a wall structure similar to that of FIG. 2A is supplemented by an additional external bag 32, which is not necessarily bonded to the main bag. In this case, the external bag provides an additional degree of leak protection, and also tends to help distribute any external contact pressure exerted by the bag.

Figure 4A:
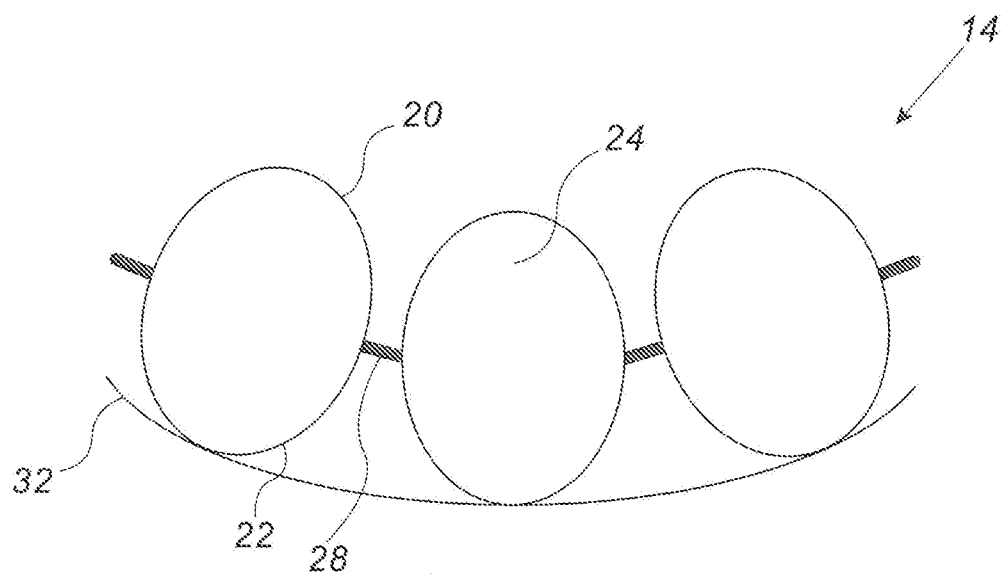
FIGS. 4A and 4B are schematic partial cross-sectional views taken through a wall of the device of FIG. 1A illustrating a further two variant implementations of a wall structure.
Figure 4B:
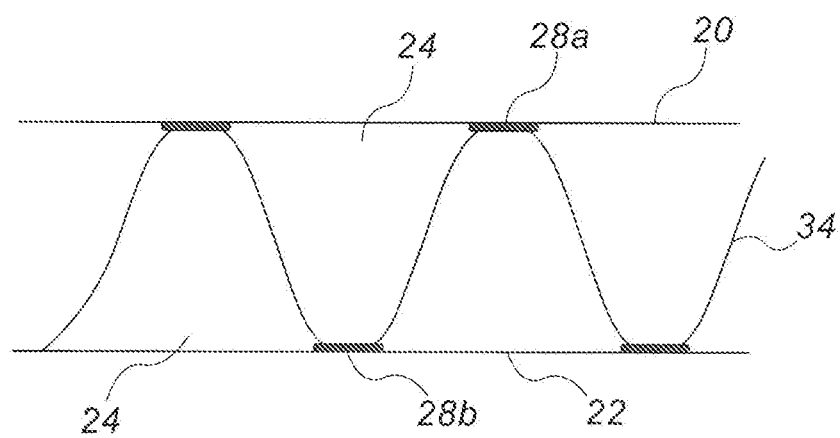

A further particularly preferred exemplary implementation is illustrated schematically in FIG. 4B. In this case, the inner and outer layers 20 and 22 are supplemented by an intermediate layer 34. Spaced apart connection regions 28a between inner layer 20 and intermediate layer 34 are interspaced between spaced apart connection regions 28b between intermediate layer 34 and outer layer 22. The result of this structure is that the connection regions are staggered and that each connection region occurs at a location that a wall cavity region is provided between the other layers, thereby providing continuous cavity-wall protection that cannot be accidentally breached without puncturing an inflatable volume of the structure. The inflatable volumes on both sides of the intermediate layer 34 may be two independent inflatable volumes, or may be interconnected at some location in the bag, either by an aperture or apertures formed through the intermediate layer or by terminating the intermediate layer just short of a boundary of the wall.

Manufacture of a wall structure such as that of FIG. 4B can be achieved using techniques known in the art. For example, inserts, such as insulating strips or other forming elements, may be inserted between a first layer and a second layer prior to welding the two layers together along lines, or dots or dashes spaced along lines, between the inserts. A third layer is then superimposed over that structure and the second and third layers are bonded along lines, dots or dashes overlying the inserts. The inserts are then withdrawn.

In all of the implementations described herein, the pattern of connection regions 28 is not necessarily uniform over the area of the walls, and may advantageously be implemented with patterns that enhance various properties of the deployed inflated bag and/or the sequence in which it deploys. By way of one example, in implementations of the invention which have a defined crease line (which may be a seam) along which the bag is folded or otherwise closed against itself when deflated, the configuration of connection regions between the layers may advantageously define elongated inflatable deployment cavities 36 extending along at least part of the crease line within two facing portions of the wall. As a result, on inflation of the bag walls, the inflatable deployment cavities 36 press against each other so as to tend to open up the internal volume of the containment compartment.

Similarly, the spaced-apart connection regions 28 may advantageously be deployed so as to define elongated inflatable boundary cavities 38 which extend so as to circumscribe a majority of opening 18 such that, on inflation of the bag 12, inflatable boundary cavities 38 tend to open up opening 18, thereby facilitating introduction of tissue into the bag.

Additionally, or alternatively, inflatable deployment cavities 36 and inflatable boundary cavities 38 may be arranged to form a framework running in one or more directions through bag 12 so as to enhance deployment of bag 12 into a desired form. Typically, the regions between these enlarged cavities have more closely spaced connection regions 28, thereby defining a "quilt" like effect, i.e., an array of smaller cavities forming a corresponding array of inflated bulges in facing relation to the containment volume, thereby maintaining flexibility of the wall while still ensuring the various advantages described herein of the cavity wall structure.

Printed markings, such as ruler markings or crossed grid vertices, are preferably applied to at least some of the above bulges. The printed markings are preferably applied within a central region of each bulge, i.e., within a middle third in each dimension between the adjacent connection regions, so that after inflation the printed markings are on the region of the bulge facing generally inwards into the containment volume. These marking preferably provide a visual frame of reference for the size of tissue pieces viewed by endoscopy within the bag. Despite the isolated positioning of each marking on a separate bulge, the marking when viewed together provide a visual effect of a grid, without the confusion that would be caused by continuous lines following the contours of the inflated wall through the crevices adjacent to the regions of interconnection.

The various implementations of bag 12 described herein may be implemented with one shared inflatable volume which allows inflation of the entire device via a single connector, or may be implemented as two or more independently inflatable volumes. The provision of two or more independently inflatable volumes may be valuable in certain cases as providing structural support to the deployed bag even in the event that one of the inflatable volumes is punctured, and further allows flexibility in cases where it may be desired to deploy the device in a specific sequence, or to inflate different parts of the device to different pressures.

The presence of multiple independent inflatable volumes may result from a wall structure such as that illustrated in FIG. 4B, from a bag structure in which two separate walls are interconnected around a peripheral seal line, or by various other arrangements of the interconnection regions that are designed to define distinct inflatable volumes. One further example is illustrated schematically in FIG. 8, where in addition to a pattern of dot-like interconnection regions, an arrangement of seal-line interconnections are configured to define an interdigitated arrangement of inflatable volumes 24a, 24b that are selectively and independently inflatable via corresponding inflation channels 40.

According to certain preferred implementations of the present invention, each inflation channel of device 10 is provided with a check valve so that, once inflated, the inflatable volumes remain pressurized without constant connection to a source of pressure. Any type of check valve may be used, including but not limited to a duckbill valve 41 such as is illustrated in a closed and open state, respectively, in FIGS. 9A and 9B. Advantageously, the check valve(s) may be integrated with connection ports 26a, 26b. In certain cases, where it is desired to perform quantitative monitoring of pressure variations within the inflatable volume(s) during a procedure, tubing 43 to support connection of a pressure sensor may be connected to the check valve, or a pressure sensor may be integrated with the check valve, as illustrated schematically in FIG. 9C. Where a qualitative indication of maintaining inflation pressure is considered sufficient, the pressure sensor may be replaced by a pressure indicator, such as a mechanical pressure sensor device which with an indicator rotor which reveals different colors according to the current pressure, or a coiled-finger indicator in which a finger-like branch tube is biased to a coiled state by an elongated leaf spring, and is extended by pressure within the branch tube while pressure is maintained above a given threshold target pressure. The pressure indicator is deployed in fluid interconnection with the inflatable volume, and generates a visible and/or audible indication when a pressure within the inflatable volume decreases or falls below a reference pressure value, which may be a fixed pressure value, or may be a reference value defined by the pressure in another volume, such as in the abdominal cavity outside the bag. Optionally, such a sensor may be provided with a battery used to generate the visible or audible indication.

A primary application of device 10 is for providing an isolated intra-body containment volume from which tissue can be removed in a bitwise or otherwise reduced-dimension manner with enhanced protection from seeding of diseased tissue or cells within the body. In order to provide a sealed access channel for removing tissue, bag 12 preferably includes an access sleeve 42 sealingly connected to opening 18. Access sleeve 42 is typically introduced in a rolled or concentrically folded configuration so as to be collapsed against opening 18, and is extended, typically by pulling on a deployment thread 47, after the tissue to be removed has been inserted into the containment volume. Access sleeve 42 is then deployed through an incision or body orifice to form a sealed working channel from the containment volume to outside the body for performing a tissue reduction process on the tissue.

Figure 14:
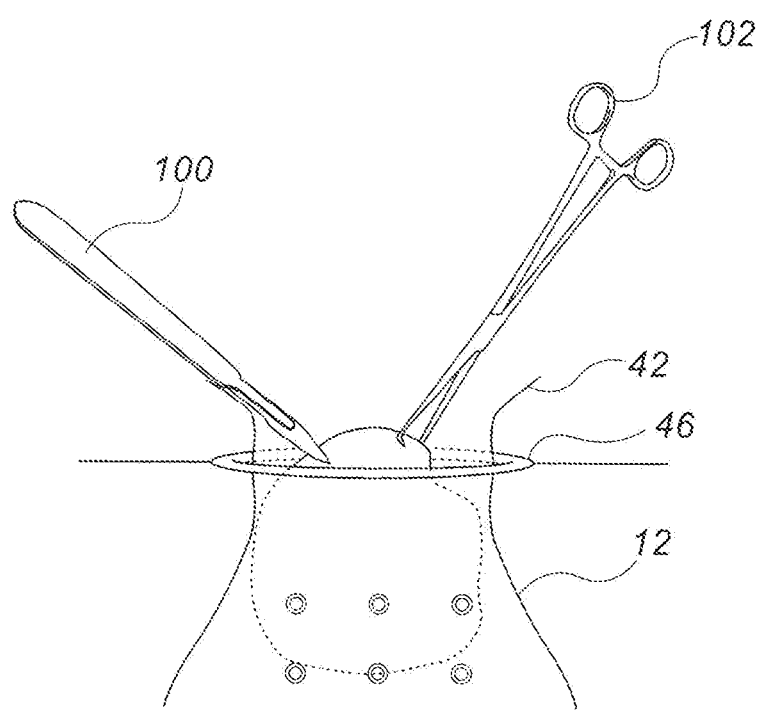
FIG. 14 illustrates schematically performance of a manual tissue reduction procedure via an abdominal incision employing a device according to the teachings of the present invention.
Figure 15:
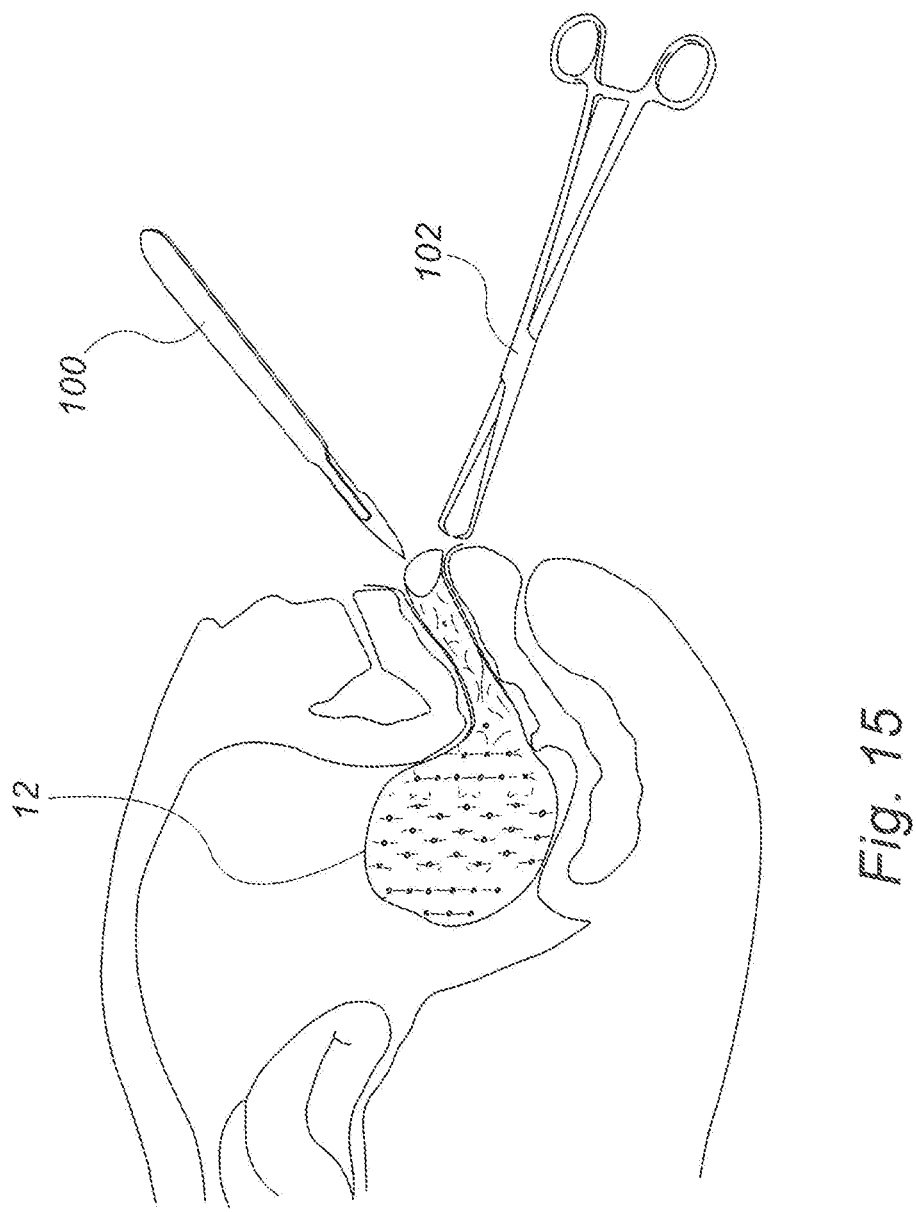
FIG. 15 illustrates schematically performance of a manual tissue reduction procedure performed vaginally employing a device according to the teachings of the present invention.

In certain implementations of the present invention, access sleeve 42 is implemented from a layer of material without inflatable internal structure. Particularly in cases where a manual tissue reduction process is performed at an access incision as illustrated in FIG. 14, or at a body orifice as illustrated in FIG. 15, there is an increased risk of perforation of the access sleeve, and it may therefore be preferable to implement an inflatable cavity wall structure within access sleeve 42. In these latter cases, the access sleeve 42 is preferably implemented with one or more independently inflatable volume that can be inflated after introduction of the tissue into bag 12 and optionally also after correct positioning of the sleeve through the access incision or body orifice.

Figure 5:
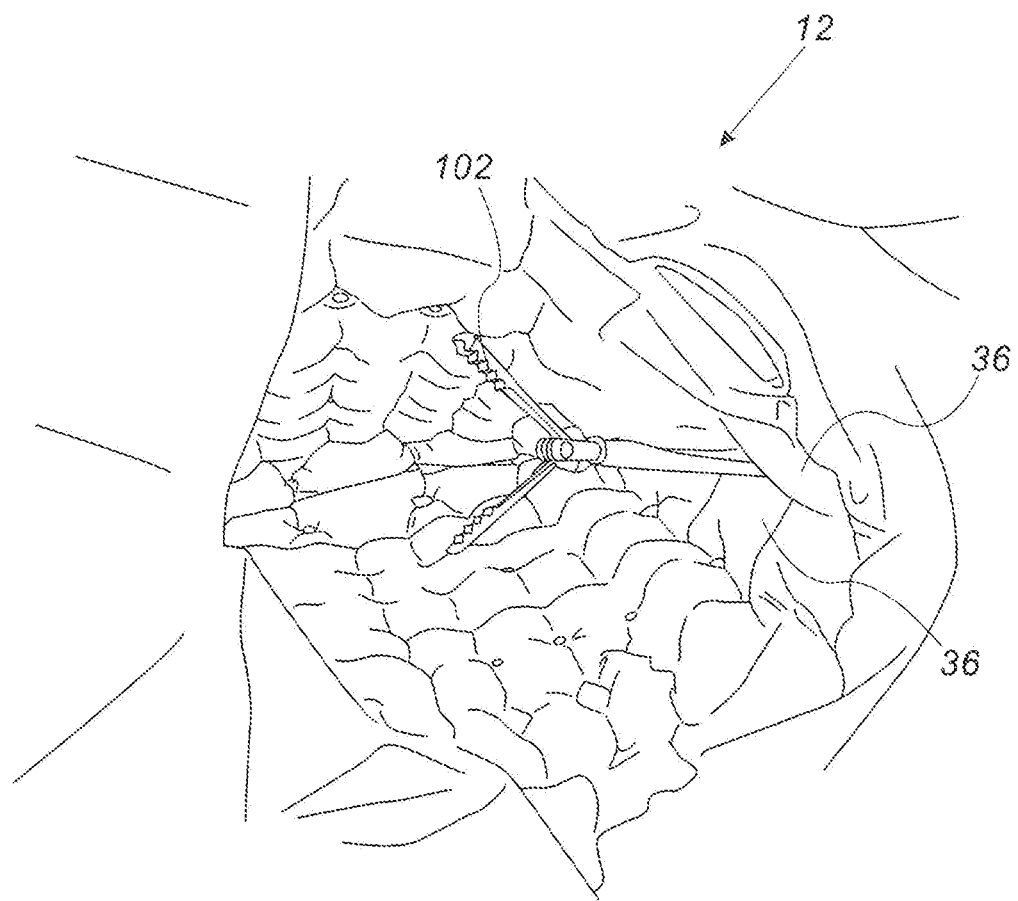
FIG. 5 is a schematic partial isometric view illustrating a tool projecting into the containment compartment of the device of FIG. 1A.
Figures 6A, 6B, 6C:
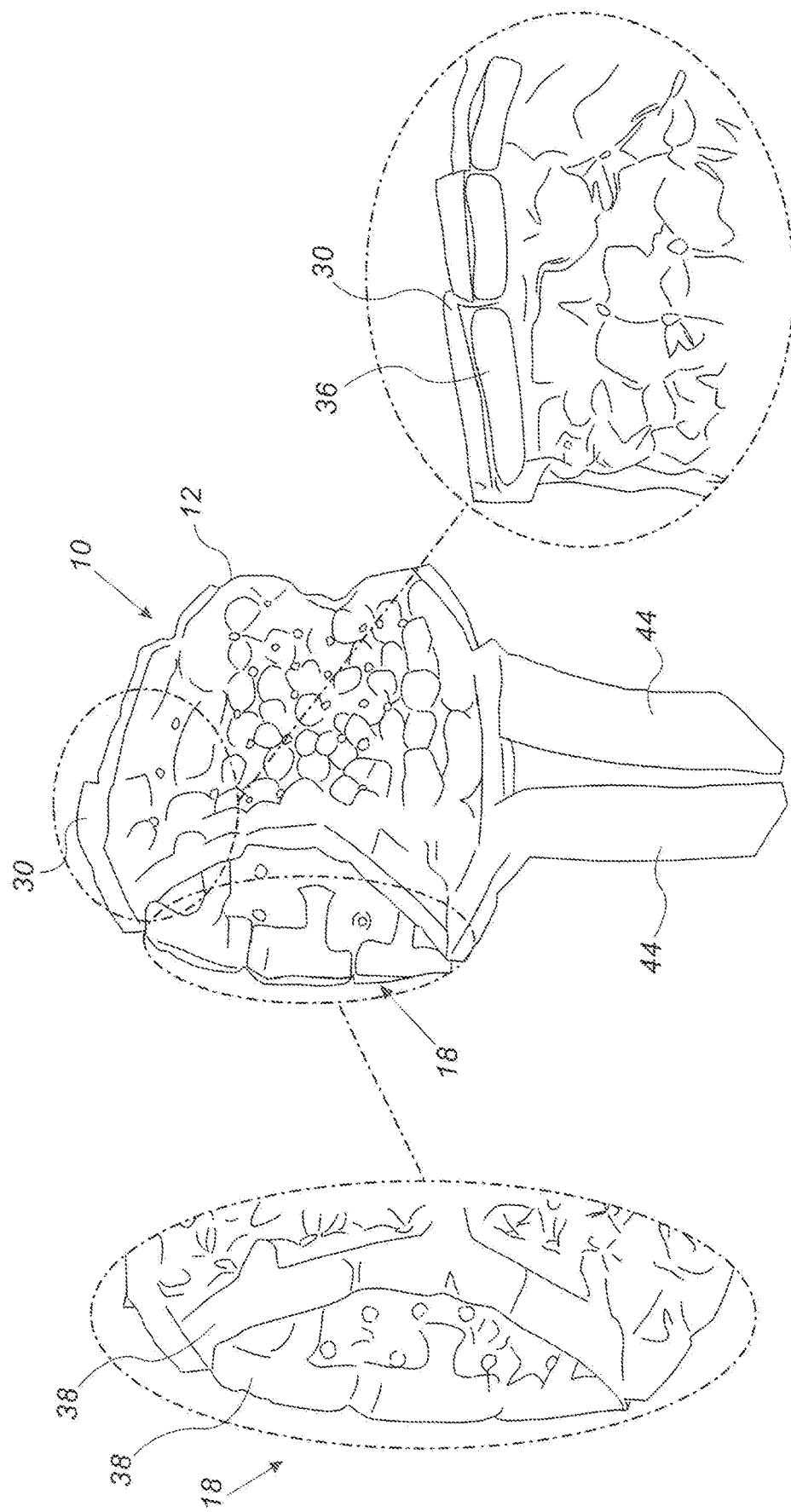
FIG. 6A is a further isometric view of the device of FIG. 1A.
FIGS. 6B and 6C are more detailed views of the regions of FIG. 6A designated by corresponding dashed ellipses.
Figure 8:
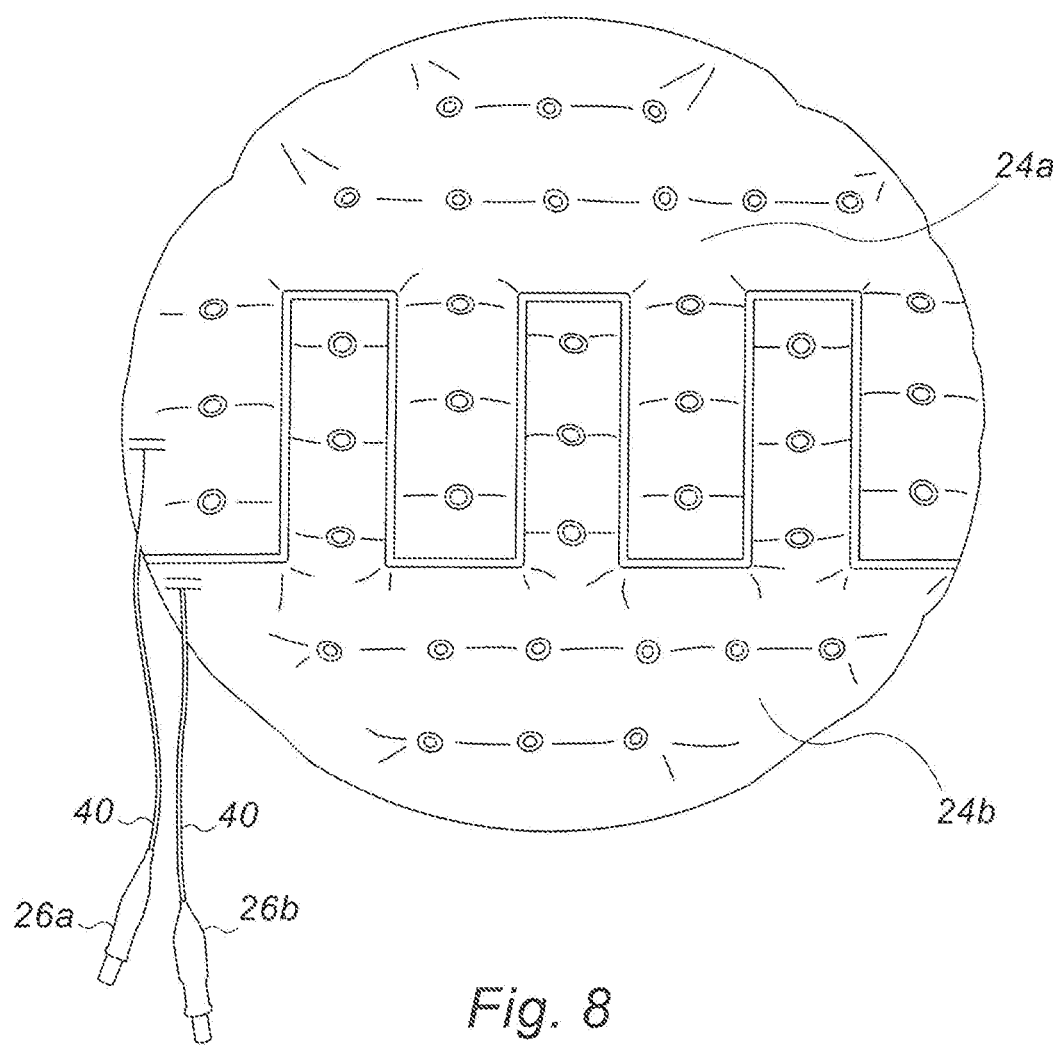
FIG. 8 is a schematic view of a variant implementation of the device of FIG. 1A showing interdigitated inflatable volumes.
Figures 9A, 9B, 9C:
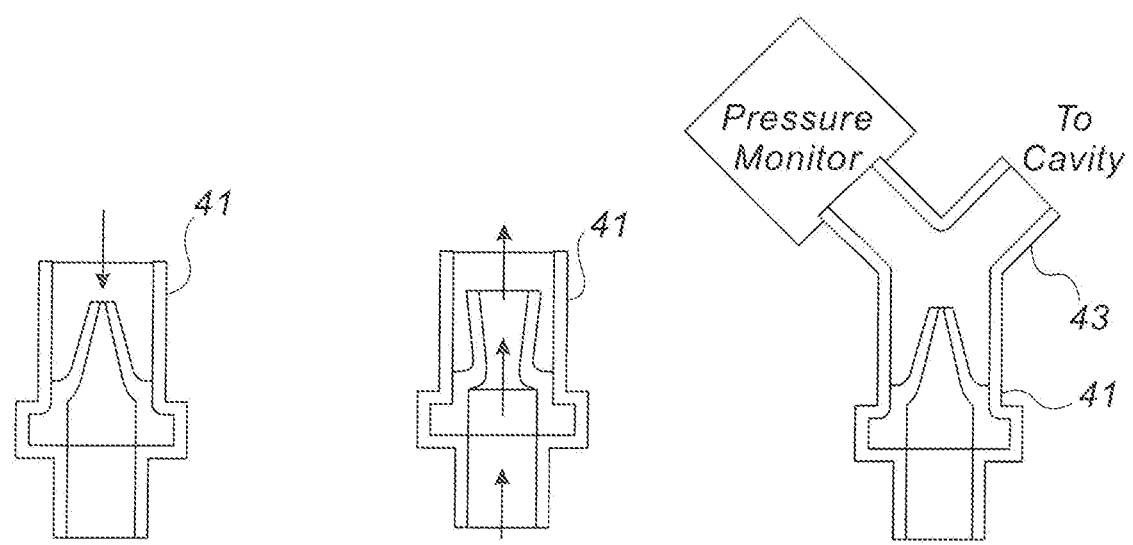
FIGS. 9A and 9B are schematic illustrations of a duckbill check valve for use with the devices of the present invention, the check valve being shown in a closed state and an open state, respectively.
FIG. 9C is a schematic illustration of the valve of FIG. 9A connected to a pressure monitor.
Figure 10A:
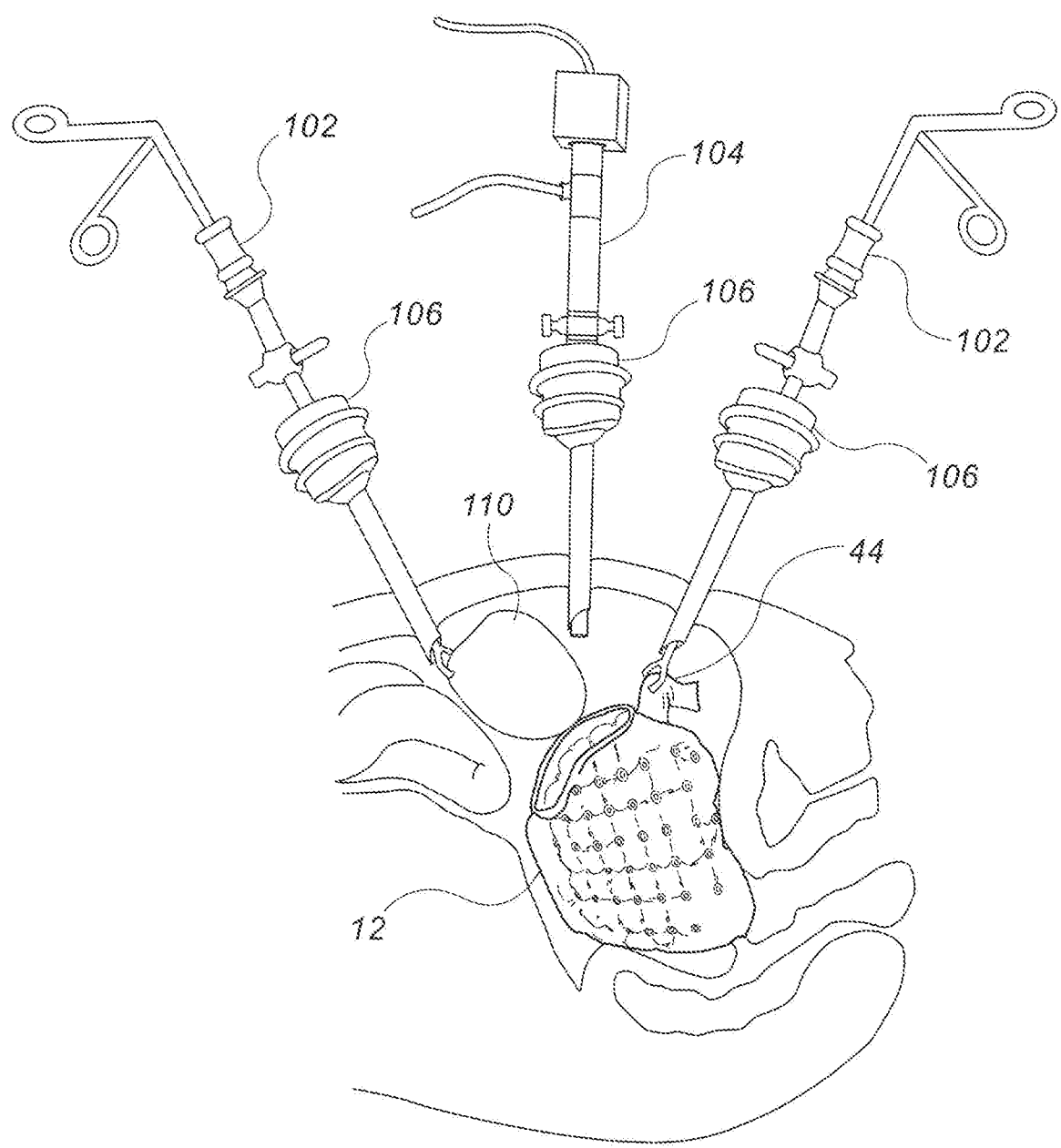
FIGS. 10A and 10B are schematic views of two stages during a gynecological procedure performed using the device of FIG. 1A.

For a fully laparoscopic tissue reduction, it is typically desired to insert one or more instruments into containment compartment 16 within bag 12. The instruments typically include a tissue reduction tool 100, such as a power morcellator, one or more gripping tools 102 for manipulating the tissue, and an endoscope 104 for visualization. In order to facilitate introduction of these instruments, bag 12 is preferably provided with one or more instrument insertion branches 44, each implemented as a flexible access tube communicating with containment compartment 16, to allow instrument access via a minor incision in a direction angularly spaced from opening 18 of bag 12. The entry of an instrument 102 into the containment compartment via branch 44 is illustrated in FIG. 5. An overall surgical procedure employing a main access sleeve 42 and instruments inserted via two branches 44 is shown in FIGS. 10A and 10B.

Specifically, in use, after severing of the tissue to be removed, for example, uterus 110, from all connections to other tissue, the tissue is introduced via opening 18 into containment volume 16 of device 10, which has been introduced via an incision or body orifice. This process is shown in FIG. 10A. Access sleeve 42 is then extended by drawing deployment thread 47, and is withdrawn from an incision in the abdominal wall after removal of the corresponding insertion trocar. Where instrument insertion branches 44 are to be used, they are retrieved through corresponding incisions, also after removal of any trocar.

Figure 12:
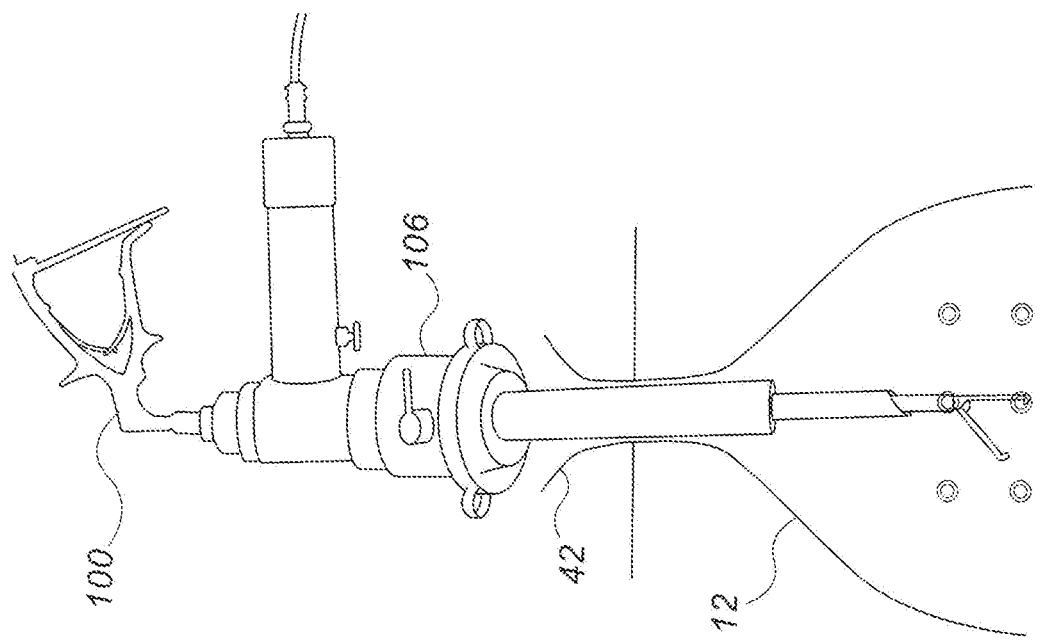
FIGS. 11 and 12 are two schematic illustrations showing different modes of anchoring of the access sleeve at an abdominal incision, without and with use of a trocar, respectively.
Figure 16:
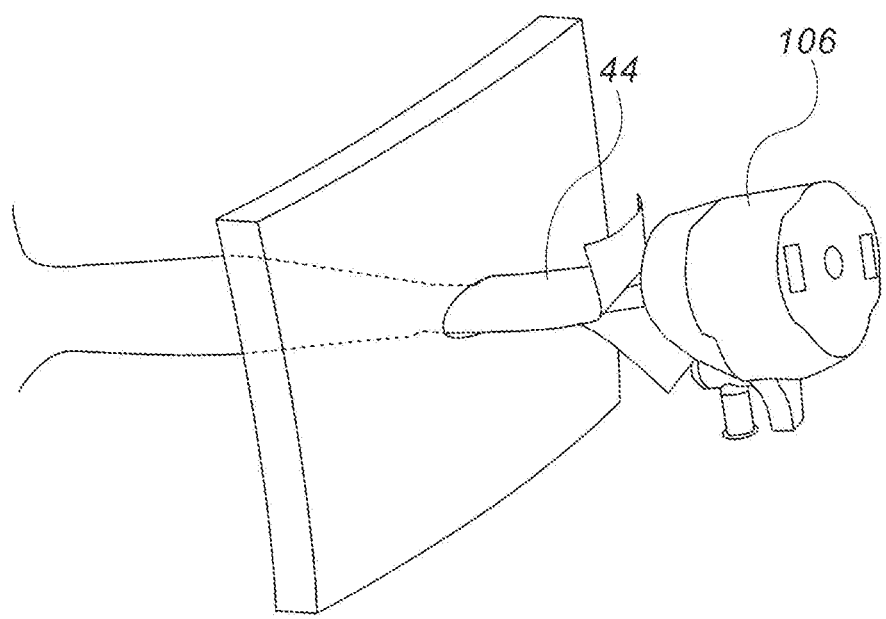
FIG. 16 illustrates schematically an instrument insertion branch of the device of FIG. 1A anchored within an abdominal incision employing a trocar.

Optionally, access sleeve 42 may then be secured by reinsertion of the trocar within access sleeve 42, as illustrated in FIG. 12. Alternatively, access sleeve 42 may be secured by stretching it around a ring template 46, as illustrated in FIG. 11. Instrument insertion branches 44 may also be used with or without insertion of a trocar within the branch sleeves, where FIG. 16 illustrates the option of reinserting the trocar 106 into the branch sleeve 44. The resulting tool deployment, ready for tissue reduction and removal, is illustrated in FIG. 10B.

Figure 10B:
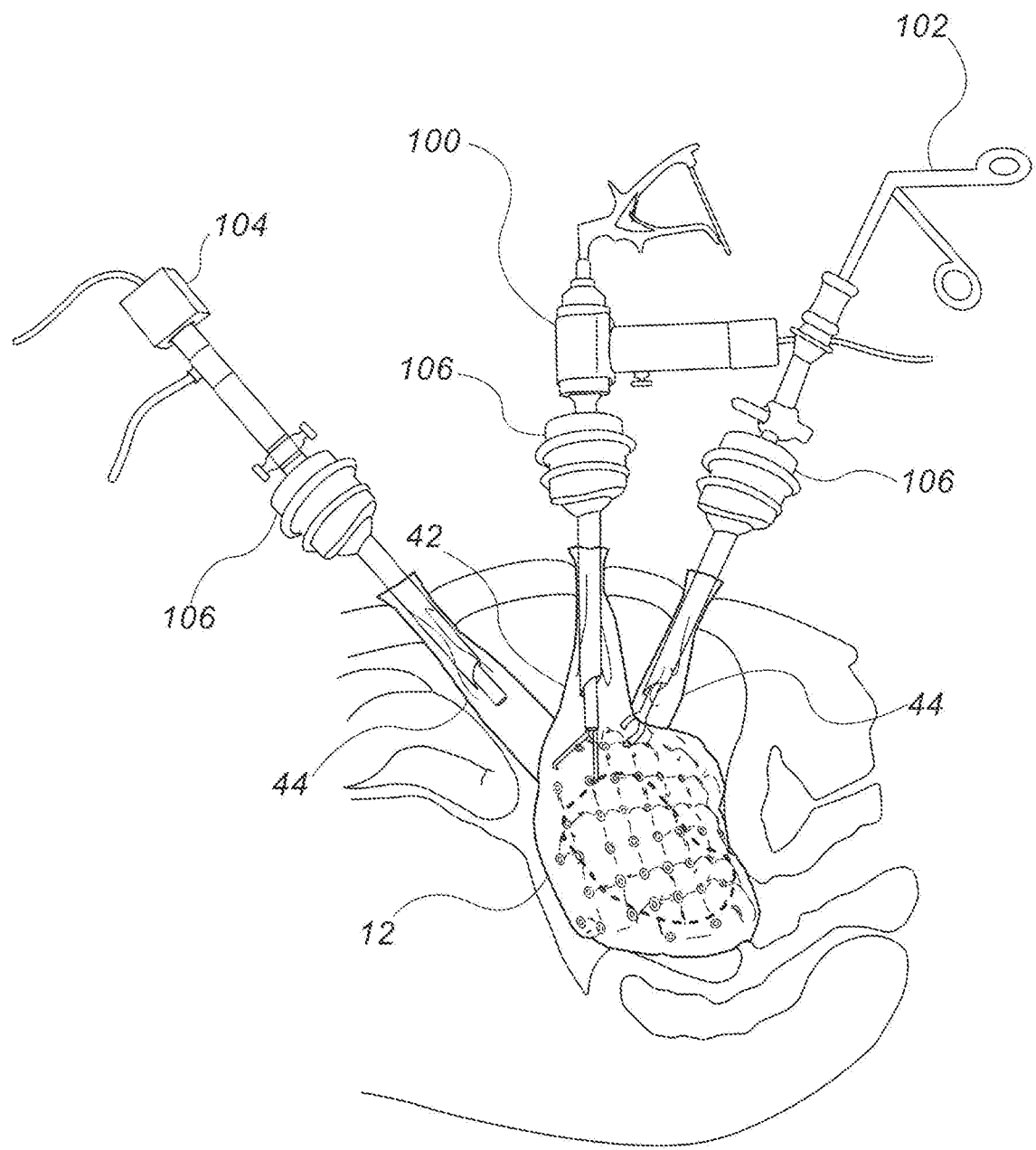
Figure 11:
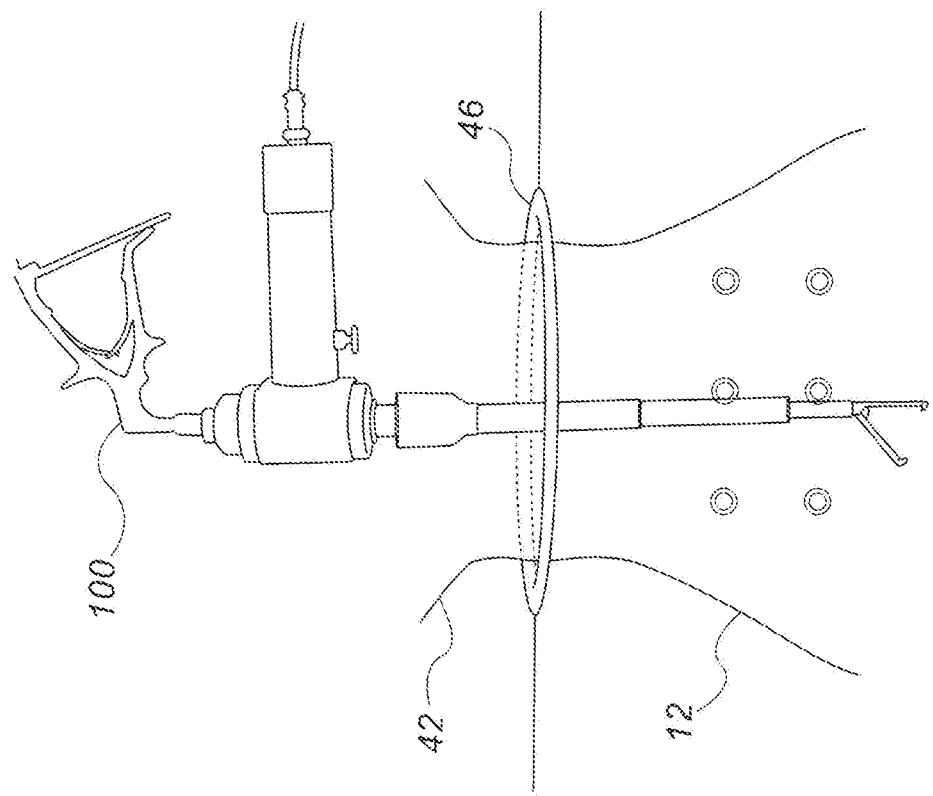
Figure 17:
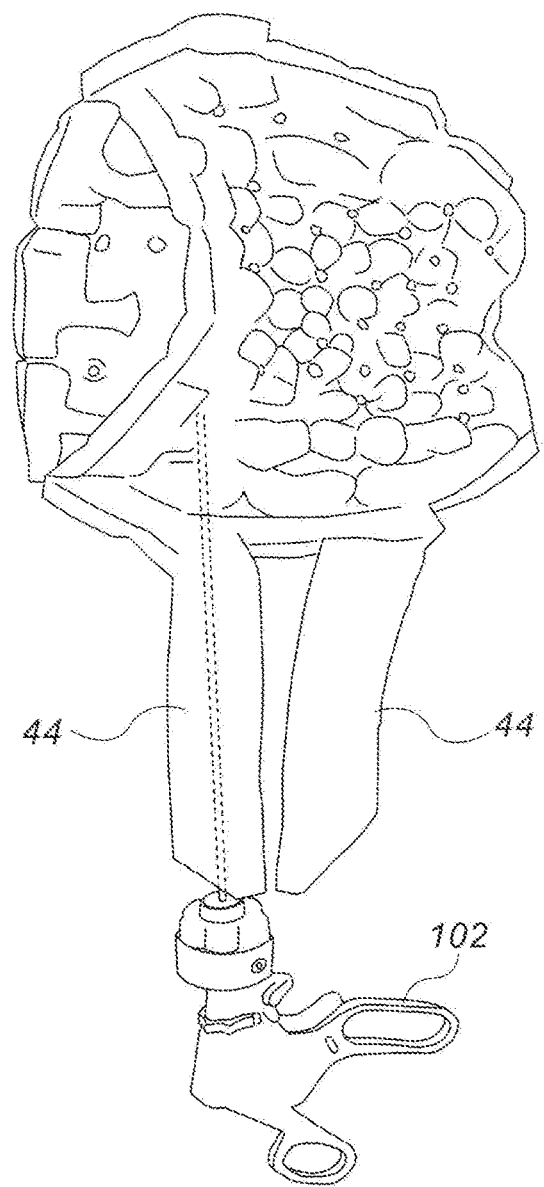
FIG. 17 is a schematic isometric view illustrating deployment of a gripping tool via an instrument insertion branch to access the containment compartment of the device of FIG. 1A.
Figure 18:
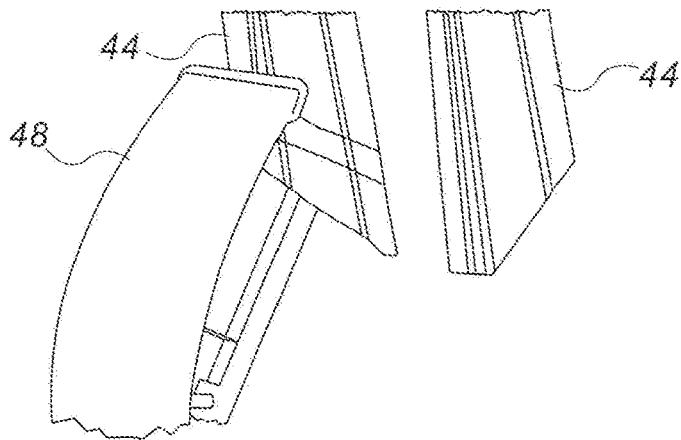
FIG. 18 illustrates schematically a branch sealing operation employing a sealing tool to seal an instrument insertion branch.

As mentioned previously, instrument insertion branches 44 are advantageously used to provide access for instruments during the procedure, as illustrated in FIGS. 5, 10B and 17. After completion of a tissue reduction process and removal of the tissue via access sleeve 42, instrument insertion branches 44 are preferably sealed before being reintroduced into the body, for removal together with the rest of device 10, typically via the primary incision (or body orifice). The sealing of branches 44 helps to insure that any contaminated tissue or cells present within containment volume 16 do not leak out into the abdominal cavity when the branches are reintroduced into the body.

When implemented using thermoplastic materials, according to certain particularly preferred implementations of the invention, branches 44 can advantageously be sealed prior to reintroduction into the body by use of a sealing tool 48 (FIG. 18) to apply heat and/or pressure so as to form one or more welded seal line across the branch 44. In a particularly preferred implementation, the extremity of the branch is turned in on itself so that only uncontaminated external surfaces are exposed, and these surfaces are then welded together using the sealing tool 48. Sealing tools commercially available for domestic applications, such as for sealing plastic storage bags, have been found to be highly effective for this purpose, rendering the branch tubes watertight, and thus certainly impervious to any potential biological contaminants (such as cancerous cells) within the containment volume.

Optionally, instrument insertion branch 44 is formed by an extension of at least one of the layers from each of two regions of wall 14 interconnected so as to form a collapsible tube. The collapsible tube configuration lends itself particularly well to the aforementioned sealing functionality.

It will be noted that device 10 may also be used to advantage in manual tissue reduction procedures, where the tissue to be removed is manipulated to be directly accessible via an access incision, and is reduced by using tissue reduction tools 100, such as scalpels, at or near the incision. FIG. 14 illustrates such a procedure performed via an abdominal incision, while FIG. 15 illustrates a similar procedure performed vaginally. In these cases, when it is not intended to introduce any additional implements into bag 12, an implementation of device 10 which does not include branches 44 may be used.

During the procedure, while device 10 is deployed, it may be desired to perform insufflation of the abdominal cavity in addition to inflation of the device wall. Where trocars are used within access sleeve 42 and/or instrument insertion branches 44, the normal inflation ports of the trocars are typically located within the sleeves/branches, and so are not in fluid flow connection with the abdominal cavity for insufflation thereof. A number of different options may be used for performing abdominal cavity insufflation, as illustrated schematically in FIGS. 13A-13C. In an implementation such as in FIG. 11 where device 10 is used without reinsertion of a trocar and access sleeve 42 is secured by stretching it around a ring template 46, an insufflation pressure supply tube 50 may be integrated with, or otherwise associated with, ring template 46, as shown schematically in FIG. 13A, for connection to a source of insufflation pressure. Where a trocar is used, such as is illustrated in FIG. 12, insufflation pressure may be provided via an insufflation pressure supply tube 50 integrated with, or otherwise associated with, an external surface of access sleeve 42, or via an insufflation port formed in a dedicated collar 45 surrounding the anchoring region of the trocar external to sleeve 42. The options of FIGS. 13A and 13B can equally be implemented at secondary incisions where instrument access branches 44 are deployed. A further option is to provide insufflation pressure via an additional incision that is not being used for instrument insertion. In this case, the incision should be sealed by a plug element 52 with an insufflation port 54 (FIG. 13C), but should not have any element projecting significantly into the abdominal cavity in order to avoid presenting a puncture hazard for bag 12.

In certain implementations, particularly where access to sleeve 42 is provided via a trocar, it may be desired to additionally provide insufflation pressure to the containment compartment volume and/or to measure a current pressure within the containment compartment. Fluid connection to the interior of bag 12 may be achieved either via a connection tube (not shown) associated with an internal surface of access sleeve 42 or via a suitably configured trocar insufflation port.

Certain particularly preferred implementations of a system employing device 10 include various pressure sensors and associated logic circuitry for monitoring fluid pressure within the inflatable volumes of device 10, and optionally also within the abdominal cavity and/or within the containment compartment, and for determining and acting on various malfunction indications. Structurally, the system preferably includes a pressure sensor $P_1$ associated with each independently inflatable volume of device 10, and preferably also a sensor $P_2$ for sensing pressure within the abdominal cavity external to the bag and $P_3$ for pressure within the containment compartment, if maintained at pressure (FIGS. 13A and 13B). The various pressure sensors are preferably connected to logic circuitry 56 configured for implementing various monitoring algorithms described below with reference to FIG. 20. Logic circuitry 56 may be implemented as custom hardware using digital or analogue circuitry, or may be implemented using a general-purpose processing system configured by suitable software, or any combination thereof, as will be clear to a person having ordinary skill in the art. The logic circuitry may additionally control valves and/or regulators 58 for directly controlling supply of pressurized fluid to one or more of the pressurized volumes, and/or may have a user interface 59 for providing audible and/or visual outputs indicative of various malfunction conditions, or conditions likely to lead to malfunction.

Figure 20:
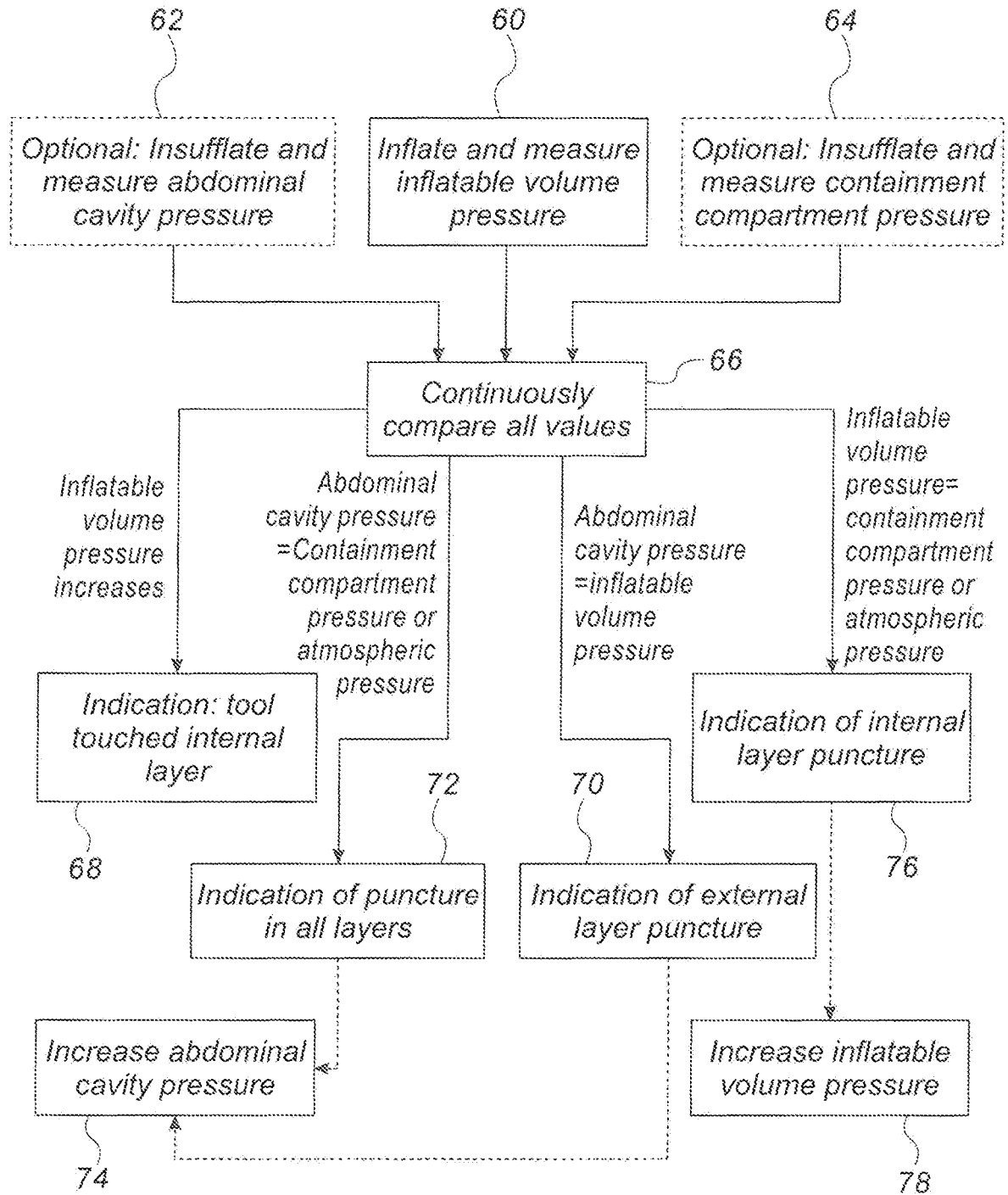
FIG. 20 is a flow diagram illustrating an aspect of operation of a system including the device of FIG. 1A according to a further aspect of the present invention.

Referring to FIG. 20, the pressure control flow chart illustrates initial steps of supplying inflation pressure to the inflatable volume(s) of device 10 (step 60), as well as insufflation of the abdominal cavity (step 62) and/or containment compartment (step 64) as relevant. The pressure of each inflated volume is then monitored at step 66 to identify various malfunction, or pre-malfunction, indications.

If the pressure within the inflatable volume, or one of the inflatable volumes, of device 10 increases, this indicates that an object is pressing against a wall of the bag, which may be a tool within the bag at risk of causing puncture. In such a case, logic circuitry preferably actuates a suitable indication (e.g., an audible buzzer or verbal message, or a visual flashing light and/or information display) at step 68.

During normal operation, the internal inflatable volume(s) of device 10 are typically maintained at a higher pressure than a pressure of the abdominal cavity. If the pressures of the inflatable volume(s) and the abdominal cavity become equalized, the system identifies that an external layer of the bag wall has been punctured (step 70). As a variant of this case, if the pressure is also equalized to the inside of the bag (in a case where the containment compartment pressure is monitored), this indicates puncturing of all layers (step 72). In either of these cases, a corresponding audio and/or visual indication is preferably generated and, in cases where automated pressure regulation is available, pressure is preferably increased in the abdominal cavity in order to create a pressure gradient inwards through the puncture (step 74), thereby tending to inhibit leakage of tissue or fluids from the containment compartment outwards. The walls of the bag, once deployed, will support a small pressure differential from outside to inside the bag. Where the bag includes more than one independently inflatable volume, a non-punctured inflatable volume may provide sufficient structural support to withstand a relatively larger external pressure, thereby allowing for enhanced pressure-differential anti-leak protection.

Finally, in a case in which the inflatable volume pressure becomes equalized with the containment compartment pressure, or with atmospheric pressure, this is identified as an indication of puncturing of an internal layer of the bag wall (step 76). In this case, in addition to a corresponding audio and/or visual indication, where automatic inflation control is available, the logic circuitry will typically supply additional inflation pressure to the inflatable volume (step 78) in an attempt to maintain at least partial inflation pressure within the bag wall despite the leak.

It should be noted that the above functionality is considered to be applicable broadly in the context of otherwise conventional tissue containment bags which lack the cavity wall structure of bag 12 of the present invention. Thus, in a conventional tissue containment bag, for example, which is supported by a collapsible or inflatable frame, the device may be used under conditions of a small pressure differential between the abdominal cavity pressure outside the bag and a volume within the bag. Optionally, the volume within the bag may be open to the atmosphere and unmonitored. Alternatively, the internal volume may also be insufflated and the pressure monitored, but maintained at a slightly different level, preferably lower, than the abdominal cavity pressure outside the bag. In the event of a sudden loss of abdominal cavity pressure, or equalization of the pressure inside and out, logic circuitry identifies a malfunction (puncture) condition, and preferably notifies the medical practitioner. Additionally, or alternatively, the logic circuitry may actuate a source of insufflation pressure and/or a system of valves connected to such a source, in order to try to maintain a pressure differential from outside the bag to within the bag, thereby tending to inhibit leakage of biological matter from the bag.

While the above options of quantitative measurement of pressure in multiple volumes provide advantageous functionality, such as that already described, it should be noted that the device of the present invention may also be used to advantage employing pressure monitoring for only the internal inflatable volumes of device 10, or even without any distinct arrangement for pressure monitoring, for example, relying on manual determination by a practitioner as to whether the internal pressure has been maintained or not by pressing manually on an exposed region of the inflatable structure. In certain preferred implementations, a visual indication is provided to the practitioner, such as by an inflatable element which changes size or shape according to whether the pressure is within a target range or falls below (or in some cases above) the target range, or a mechanical pressure sensor which provides a visual and/or audible output indicative of whether the pressure falls within the target range.

Figure 19B:
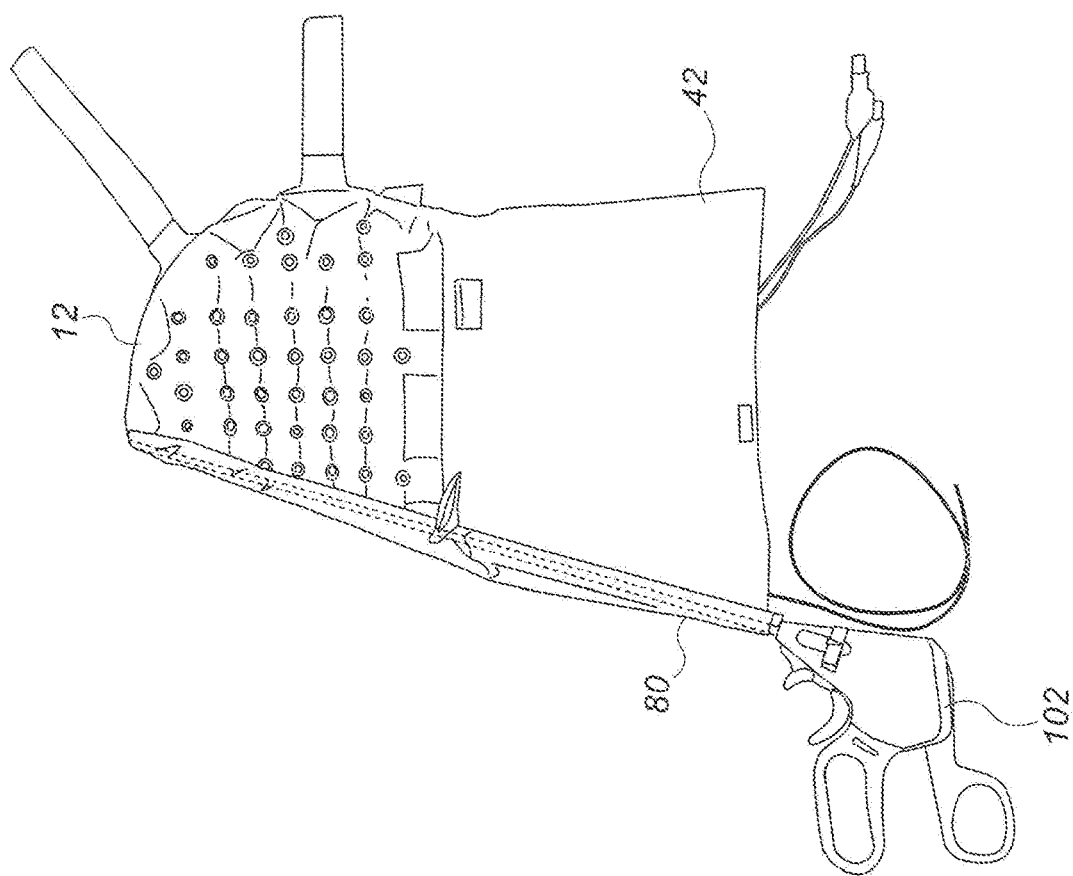
FIGS. 19A and 19B are schematic illustrations showing two stages in a procedure for compacting the device of FIG. 1A.
Figure 19A:
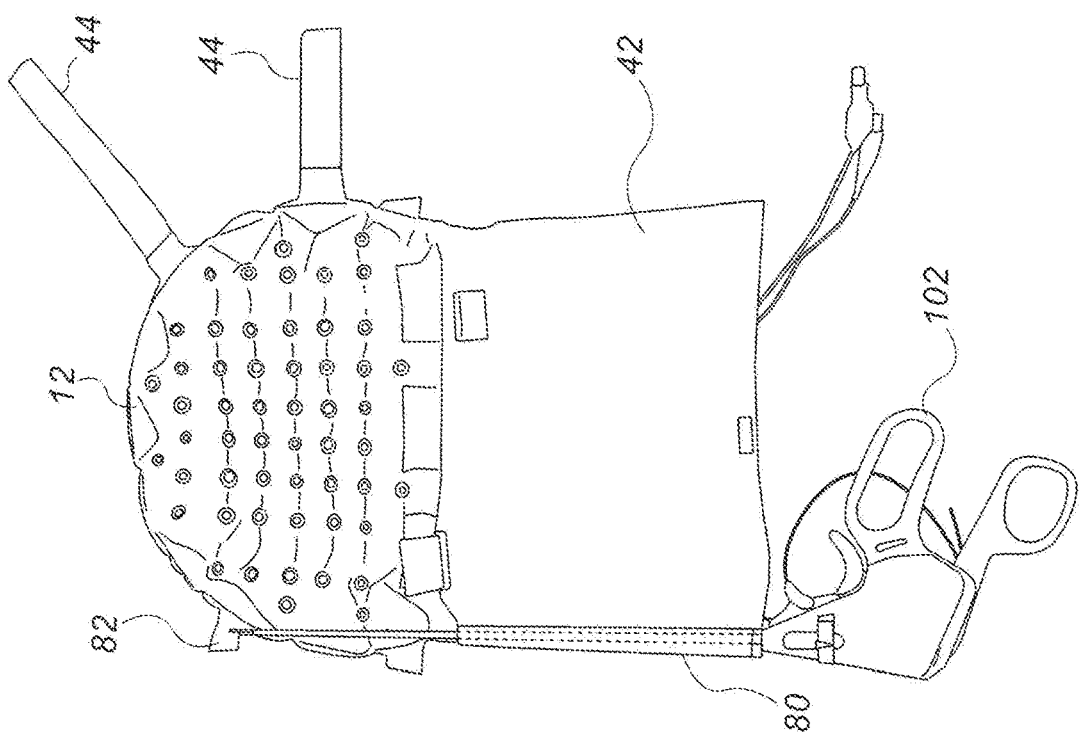

On completion of the tissue reduction and removal process, pressure is preferably released from the inflatable volume(s) of device 10, such as by neutralizing or removing the check valves, as is known in the art. Optionally, active suction can be used to ensure that the thickness of the device walls is reduced as much as possible. The device is then preferably compacted to facilitate removal from the body. According to one particularly preferred approach, illustrated in FIGS. 19A and 19B, for compacting the device for removal, bag 12 is provided with at least one loop element 80, deployed on an external surface of the device. Loop element 80 is located and configured to facilitate rolling of the bag by insertion of an instrument through the loop element and rotation of the instrument. The term "loop" is used here to refer to any structure which forms a closed loop around a shaft of an instrument, and may be either a localized loop or an extended structure which is effectively a tube or sleeve. In the example illustrated here, the loop element 80 is implemented as an elongated sleeve passing along an external surface of access sleeve 42. When the practitioner is ready to remove the device, she inserts a gripper tool 102 through the sleeve of loop element 80 and then grips part of the bag, preferably via a projecting tab 82, as shown in FIG. 19A. Subsequent rotation of the gripper tool about its direction of elongation results in rolling of the bag around the tool, as shown in FIG. 19B. Once fully rolled, the gripper tool can be removed together with the rolled device via the primary incision.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

It will be appreciated that the above descriptions are intended only to serve as examples, and that many other embodiments are possible within the scope of the present invention as defined in the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A tissue containment device for isolating tissue from surrounding tissue during an intra-body surgical procedure, the device comprising:
 a bag comprising one or more walls, defining a containment compartment having an internal volume and an opening for accessing said internal volume, wherein said one or more walls are formed from at least two layers comprising an inner layer and an outer layer, and a plurality of connection regions between said inner layer and said outer layer; wherein said inner layer faces said internal volume of said containment compartment, and said outer layer faces outwards from said bag, wherein said plurality of connection regions between the at least two layers define adjacent elongated inflatable deployment cavities, each of the inflatable deployment cavities comprising an inflatable volume; wherein in a pair of adjacent inflatable volumes of said inflatable deployment cavities, a first inflatable volume of said pair of adjacent inflatable volumes is located at an opposite side of a connection region of the plurality of connection regions, from a second inflatable volume of said pair of adjacent inflatable volumes, and at least one inflation port in fluid connection with said inflatable volumes for introducing and removing a fluid to and from said inflatable volumes, wherein said device is configured to be introduced in a compact uninflated state into a body cavity through a laparoscopic incision, and wherein said inflatable volumes are configured to be inflated inside said body cavity;

wherein said elongated inflatable deployment cavities are configured such that, when the fluid is introduced to said inflatable volumes, said adjacent elongated inflatable deployment cavities are inflated and press against each other when said device is deployed inside the body cavity of a subject body to form an inflatable volume structurally supporting a larger pressure outside the bag relative to pressure inside the internal volume of said containment compartment defined by the one or more walls of said bag, and to isolate tissue in said internal volume from tissue in said body cavity facing said outer layer, when said opening is outside said subject body.

2. A device according to claim 1, wherein said adjacent elongated inflatable deployment cavities surround said internal volume.

3. A device according to claim 2, wherein said adjacent deployment cavities are positioned vertically around all of said internal volume to provide a structure in which the at least two layers are separated by a fluid-filled cavity.

4. A device according to claim 1, wherein said at least two layers are implemented as initially flat sheets of material that are selectively interconnected at said plurality of connection regions.

5. A device according to claim 1, wherein at least one layer of said at least two layers is implemented as a layer having an increased resistance to flexing compared to a different layer of said at least two layers.

6. A device according to claim 1, wherein at least one layer of said at least two layers differs from a different layer of said at least two layers in at least one property selected from the group consisting of: shear strength, burst limit and puncture resistance.

7. A device according to claim 1, comprising an access sleeve sealingly connected to said bag and forming a sealed access channel to said internal volume.

8. A device according to claim 7, wherein said access sleeve is configured to move between a collapsed state when said tissue containment device is introduced into the body, and an extended state when said tissue containment device is deployed in said body.

9. A device according to claim 7, wherein said access sleeve is formed from a single layer of material.

10. A device according to claim 7, wherein said access sleeve is non-inflatable.

11. A device according to claim 7, comprising a ring associated with said sleeve for securing said sleeve in an extended state.

12. A device according to claim 1, further comprising a pressure indicator in fluid interconnection with said inflatable volumes, said pressure indicator being configured to generate a visible and/or audible indication when a pressure within said inflatable volumes decreases or falls below a reference pressure value.

13. A device according to claim 1, comprising at least one instrument insertion branch in communication with said containment compartment, wherein said at least one instrument insertion branch is shaped as an access sleeve and is configured to allow instrument access into said containment compartment.

14. A device according to claim 13, wherein said at least one instrument insertion branch is formed by an extension of at least one layer of said at least two layers.

15. A device according to claim 13, wherein said at least one instrument insertion branch is coupled to said bag at a location spaced apart from said opening.

16. A device according to claim 13, wherein said at least one instrument insertion branch is flexible.

17. A device according to claim 1, further comprising:
a pressure monitoring system comprising: a pressure sensor deployed for sensing a pressure within the inflatable volumes.

18. A device according to claim 17, further comprising:
a logic circuitry in communication with the pressure sensor and configured to monitor variations in the pressure within the inflatable volumes to determine whether the variations are indicative of a malfunction condition of the bag.

19. A device according to claim 1, wherein said opening for accessing said internal volume is a single opening.

20. A device according to claim 19 comprising an access sleeve sealingly connected to said opening, wherein said access sleeve is configured to be introduced into said body cavity through an incision, in a rolled or folded configuration to form a sealed working channel from the internal volume to outside the body.

21. A method for deployment of a tissue containment device, comprising:
introducing a tissue containment device in a compact uninflated state into a body cavity through a laparoscopic incision, said device comprises
one or more walls, defining a containment compartment having an internal volume and an opening for accessing said internal volume, wherein said one or more walls are formed from at least two layers and a plurality of connection regions between said at least two layers; wherein said plurality of connection regions between the at least two layers define adjacent elongated inflatable deployment cavities, each of the inflatable deployment cavities comprising an inflatable volume; wherein in a pair of adjacent inflatable volumes of said inflatable deployment cavities, a first inflatable volume of said pair of adjacent inflatable volumes is located at an opposite side of a connection region of the plurality of connection regions, from a second inflatable volume of said pair of adjacent inflatable volumes and at least one inflation port in fluid connection with said inflatable volumes for introducing and removing a fluid to and from said inflatable volumes, wherein said elongated inflatable deployment cavities are configured such that, when the fluid is introduced to said inflatable volumes, said adjacent elongated inflatable deployment cavities are inflated and press against each other when said device is deployed inside said body cavity of a subject body to form an inflatable volume structurally supporting a larger pressure outside the tissue containment device relative to pressure inside the internal volume of said containment compartment defined by the one or more walls of said tissue containment device;

inflating said inflatable volumes inside said body cavity such that said adjacent elongated inflatable deployment cavities press against each other to form said inflatable volume.

22. A method according to claim 21, comprising sensing pressure in said inflatable volumes.

23. A method according to claim 21, comprising delivering an indication if pressure of said inflatable volumes is lower and/or higher than a predetermined reference value.

24. A method according to claim 21, wherein said inflating comprises inflating said inflatable volumes to reach a pressure which is higher than a pressure of the body cavity.

25. A method according to claim 24, delivering an audio and/or a visual indication if pressure within said inflatable volumes is equalized or is lower than said pressure of said body cavity.

26. A method according to claim 21, wherein said inflating comprises inflating said inflatable volumes such that said inflatable volumes surround said internal volume.

27. A method according to claim 21, comprising inserting tissue from said body cavity into said internal volume prior to said inflating.

28. A method according to claim 21, comprising manipulating said tissue within said internal volume while said inflatable volumes are inflated to a pressure which is higher than a pressure of said body cavity.

* * * * *